(12) United States Patent
Satterfield

(10) Patent No.: US 10,093,966 B2
(45) Date of Patent: Oct. 9, 2018

(54) COOPERATIVE PRIMERS, PROBES, AND APPLICATIONS THEREOF

(71) Applicant: DNA Logix, Inc., Bountiful, UT (US)

(72) Inventor: Brent C. Satterfield, West Bountiful, UT (US)

(73) Assignee: DNA Logix, Inc., Bountiful, UT (US)

( * ) Notice: Subject to any disclaimer, the term of this patent is extended or adjusted under 35 U.S.C. 154(b) by 168 days.

(21) Appl. No.: 15/282,234

(22) Filed: Sep. 30, 2016

(65) Prior Publication Data

US 2017/0247752 A1    Aug. 31, 2017

Related U.S. Application Data

(63) Continuation of application No. 13/944,192, filed on Jul. 17, 2013.

(60) Provisional application No. 61/732,537, filed on Dec. 3, 2012, provisional application No. 61/672,329, filed on Jul. 17, 2012.

(51) Int. Cl.
*C12Q 1/68* (2018.01)
*C12Q 1/6832* (2018.01)
*C12Q 1/6893* (2018.01)
*C12Q 1/6853* (2018.01)

(52) U.S. Cl.
CPC ......... *C12Q 1/6832* (2013.01); *C12Q 1/6853* (2013.01); *C12Q 1/6893* (2013.01); *C12Q 2600/156* (2013.01); *C12Q 2600/158* (2013.01)

(58) Field of Classification Search
CPC ....................................................... C12Q 1/68
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,845,205 A | 7/1989 | Dinh et al. |
| 4,981,957 A | 1/1991 | Lebleu et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |

(Continued)

FOREIGN PATENT DOCUMENTS

| | | |
|---|---|---|
| WO | 2002/002817 | 1/2002 |
| WO | 2006/119326 | 11/2006 |

OTHER PUBLICATIONS

Akhras et al. (Connector Inversion Probe Technology: A Powerful One-Primer Multiplex DNA Amplification System for Numerous Scientific Applications, PLoS One. Sep. 19, 2007;2(9):e915).*

(Continued)

*Primary Examiner* — Aaron A Priest
(74) *Attorney, Agent, or Firm* — Meunier Carlin & Curfman LLC

(57) ABSTRACT

Disclosed are compositions and a method relating to amplifying and detecting nucleic acids.

8 Claims, 9 Drawing Sheets

Specification includes a Sequence Listing.

(56) References Cited

U.S. PATENT DOCUMENTS

| | | |
|---|---|---|
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,724 A | 11/1995 | Ahern |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,597,909 A | 1/1997 | Urdea et al. |
| 5,596,091 A | 2/1997 | Switzer |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,646,265 A | 7/1997 | McGee |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 6,291,669 B1 | 9/2001 | Kwiatkowski et al. |
| 6,294,664 B1 | 9/2001 | Ravikumar et al. |
| 2003/0064402 A1 | 4/2003 | Egholm |
| 2009/0098566 A1 | 4/2009 | Notomi et al. |
| 2009/0305264 A1 | 12/2009 | West et al. |
| 2010/0021904 A1 | 1/2010 | Pierce et al. |
| 2010/0055742 A1 | 3/2010 | Nakashima et al. |
| 2011/0020823 A1 | 1/2011 | Burns |
| 2012/0135473 A1 | 5/2012 | Chun et al. |
| 2012/0220468 A1 | 8/2012 | Chun et al. |

OTHER PUBLICATIONS

Akhras, M.S., et al., "Connector Inversion Probe Technology: A Powerful One-Primer Multiplex DNA Amplification System for Numerous Scientific Applications," PLoS ONE, vol. 2, No. 9, 2007, p. e195.

Beaucage, S.L., et al., "Deoxynucleoside Phosphoramidites—A New Class of Key Intermediates for Deoxypolynucleotide Synthesis," Tetrahedron Letters, vol. 22, No. 20, 1981, pp. 1859-1862.

Englisch, U., et al., Chemically Modified Oligonucleotides as Probes and Inhibitors, Angewandte Chemie, International edition in English, vol. 30, No. 6, Jun. 1991, pp. 613-629.

Gebinoga, M., et al., "Comparison of Self-Sustained Sequence-Replication Reaction Systems," European Journal of Biochemistry, vol. 235, Issues 1-2, 1996, pp. 256-261.

Hall, R.H., et al., "Nucleotides. Part XLI. Mixed Anhydrides as Intermediates in the Synthesis of Dinucleoside Phosphates," Journal of the Chemical Society, 1957, pp. 3291-3296.

Hall, J.G., et al., "Sensitive detection of DNA polymorphisms by the serial invasive signal amplification reaction," PNAS, vol. 97, No. 15, 2000, pp. 8272-8277.

Hardenbol, P., et al., "Multiplexed genotyping with sequence-tagged molecular inversion probes," Nat Biotechnol, vol. 21, No. 6, 2003, pp. 673-678, downloaded from www.genome.cship.org.

Heim, A., et al., "Highly sensitive detection of gene expression of an intronless gene: Amplification of mRNA, but not genomic DNA by nucleic acid sequence based amplification (NASBA)," Nucleic Acids Res., vol. 26, No. 9, 1998, pp. 2250-2251.

Holland, P.M., et al., "Detection of specific polymerase chain reaction product by utilizing the 5' → 3' exonuclease activity of *Thermus aquaticus* DNA polymerase," Proc. Natl. Acad. Sci. USA, vol. 88, Aug. 1991, pp. 7276-7280.

Itakura, K., et al., Synthesis and use of synthetic oligonucleotides, Ann. Rev. Biochem., vol. 53, 1984, pp. 323-356.

Iyer, R.P., et al., "3H-1,2-Benzodithiole-3-one 1,1-dioxide as an improved sulfurizing reagent in the solid-phase synthesis of oligodeoxyribonucleoside phosphorothioates," J. Am. Chem. Soc., vol. 112, No. 3, 1990, pp. 1253-1254.

Kwoh, D.Y., et al., "Transcription-based amplification system and detection of amplified human immunodeficiency virus type 1 with a bead-based sandwich hybridization format," Proc. Natl. Acad. Sci., vol. 86, 1989, pp. 1173-1177.

Lebedev, A.,"Heat-Activatable Primers for Hot-Start PCR: Oligonucleotide Synthesis and Basic PCR Setup," Current Protocols in Nucleic Acid Chemistry, Chapter 4, Unit 4.35, 2009, 17 pages.

Lesnick, E., et al., "Relative Thermodynamic Stability of DNA, RNA, and DNA:RNA Hybrid Duplexes: Relationship with Base Composition and Structure," Biochemistry, vol. 34, 1995, pp. 10807-10815.

Letsinger, R.L., et al., "Synthesis of Thymidine Oligonucleotides by Phosphite Triester Intermediates," Journal of the American Chemical Society, vol. 98, 1976, pp. 3655-3661.

Lindblad-Toh, K., et al., "Large-scale discovery and genotyping of single-nucleotide polymorphisms in the mouse," Nature Genetics, vol. 24, No. 4, Apr. 2000, pp. 381-386.

Little, M.C., et al., "Strand Displacement Amplification and Homogeneous Real-Time Detection Incorporated in a Second-Generation DNA Probe System, BDProbe TecET," Clinical Chemistry, vol. 45, No. 6, 1999, pp. 777-784.

Lizardi, P.M., et al., "Exponential amplification of nucleic acids: new diagnostics using DNA polymerases and RNA replicases," Trends in Biotechnology, vol. 9, 1991, pp. 53-58.

(56) References Cited

OTHER PUBLICATIONS

Matteucci, M.D., et al., "Synthesis of Deoxyoligonucleotides on a Polymer Support," Journal of the American Chemical Society, vol. 103, No. 11, 1981, pp. 3185-3191.

McGraw, R.A., et al., "Sequence-Dependent Oligonucleotide-Target Duplex Stabilities: Rules from Empirical Studies with a Set of Twenty-Mers," Biotechniques, vol. 8, No. 6, 1990, pp. 674-678.

Moore, D.F., et al., "Detection and Identification of *Mycobacterium tuberculosis* Directly from Sputum Sediments by Ligase Chain Reaction," Journal of Clinical Microbiology, vol. 36, No. 4, 1998, pp. 1028-1031.

Narang, S.A., et al., "Chemical Synthesis of Deoxyoligonucleotides by the Modified Trimester Method," Methods in Enzymology, vol. 65, No. 1, 1980, pp. 610-620.

Nazerenko, I.A., et al., "A closed tube format for amplification and detection of DNA based on energy transfer," Nucleic Acids Research, vol. 25, No. 12, 1997, pp. 2516-2521.

Nielsen, P.E., et al., "Sequence-Selective Recognition of DNA by Strand Displacement with a Thymine-Substituted Polyamide," Science, vol. 254, No. 5037, Dec. 6, 1991, pp. 1497-1500.

Nielsen, P.E., et al., "Peptide Nucleic Acid (PNA). A DNA Mimic with a Peptide Backbone," Bioconjugate Chem., vol. 5, 1994, pp. 3-7.

Nilsson, M., et al., "Padlock Probes: Circularizing Oligonucleotides for Localized DNA Detection," Science, vol. 265, No. 5181, Sep. 30, 1994, pp. 2085-2088.

O'Meara, Deirdre, et al., "Cooperative Oligonucleotides Mediating Direct Capture of Hepatitis C Virus RNA from Serum," Journal of Clinical Microbiology, vol. 36, No. 9, Sep. 1998, pp. 2454-2459.

Piepenburg Melting Temp, Oligo Calc, accessed online Jan. 7, 2014.

Piepenburg et al., DNA detection Using Recombination Proteins, PLoS Biol. 2006, 4(7), e204.

Pless, R.C., et al., "Solid support synthesis of oligothymidylates using phosphorochloridates and 1-alkylimidazoles," Nucleic Acids Research, vol. 2, No. 6, Jun. 1975, pp. 773-786.

Poritz, M.A., et al., "Getting Things Backwards to Prevent Primer Dimers," The Journal of Molecular Diagnostics, vol. 16, Issue 2, Mar. 2014, pp. 159-162.

Rychlik, W., et al., "Optimization of the annealing temperature for DNA amplification in vitro," Nucleic Acids Research, vol. 18, No. 21, 1990, pp. 6409-6412.

Sambrook, J., et al., "Molecular Cloning: A Laboratory Manual: $2^{nd}$ Edition," Cold Spring Harbor Laboratory Press, Cold Spring Harbor, New York, Chapters 5 and 6, 1989, 97 pages.

Sanghvi, Y.S., "Heterocyclic Base Modifications in Nucleic Acids and Their Applications in Antisense Oligonucleotides," Chapter 15, Antisense Research and Applications, CRC Press, 1993, pp. 273-288.

Schweitzer, B., et al., "Combining nucleic acid amplification and detection," Current Opinion in Biotechnology, vol. 12, Issue 1, Feb. 2001, pp. 21-27.

Thelwell, N., et al., "Mode of action and application of Scorpion primers to mutation detection," Nucleic Acids Res., vol. 28, No. 19, 2000, pp. 3752-3761.

Walker, G.T., et al., "Isothermal in vitro amplification of DNA by a restriction enzyme/DNA polymerase system," Proc. Natl. Acad. Sci. Usa, vol. 89, 1992, pp. 392-396.

Whelan, A.C., et al., "Direct Genotypic Detection of *Mycobacterium tuberculosis* Rifampin Resistance in Clinical Specimens by Using Single-Tube Heminested PCR," Journal of Clinical Microbiology, vol. 33, No. 3, 1995, pp. 556-561.

Wylie, J.L., et al., "Comparative Evaluation of Chlamydiazyme, PACE 2, and AMP-CT Assays for Detection of *Chlamydia trachomatis* in Endocervical Specimens," Journal of Clinical Microbiology, vol. 36, No. 12, 1998, pp. 3488-3491.

International Search Report and Written Opinion, dated Nov. 26, 2013, received in connection with International Application No. PCT/US2013/050811.

Supplementary Search report issued in European Application No. EP 13820614, dated Jan. 14, 2016.

Office Action Issued in Chinese Application No. 201380041220.2, dated May 5, 2016.

\* cited by examiner

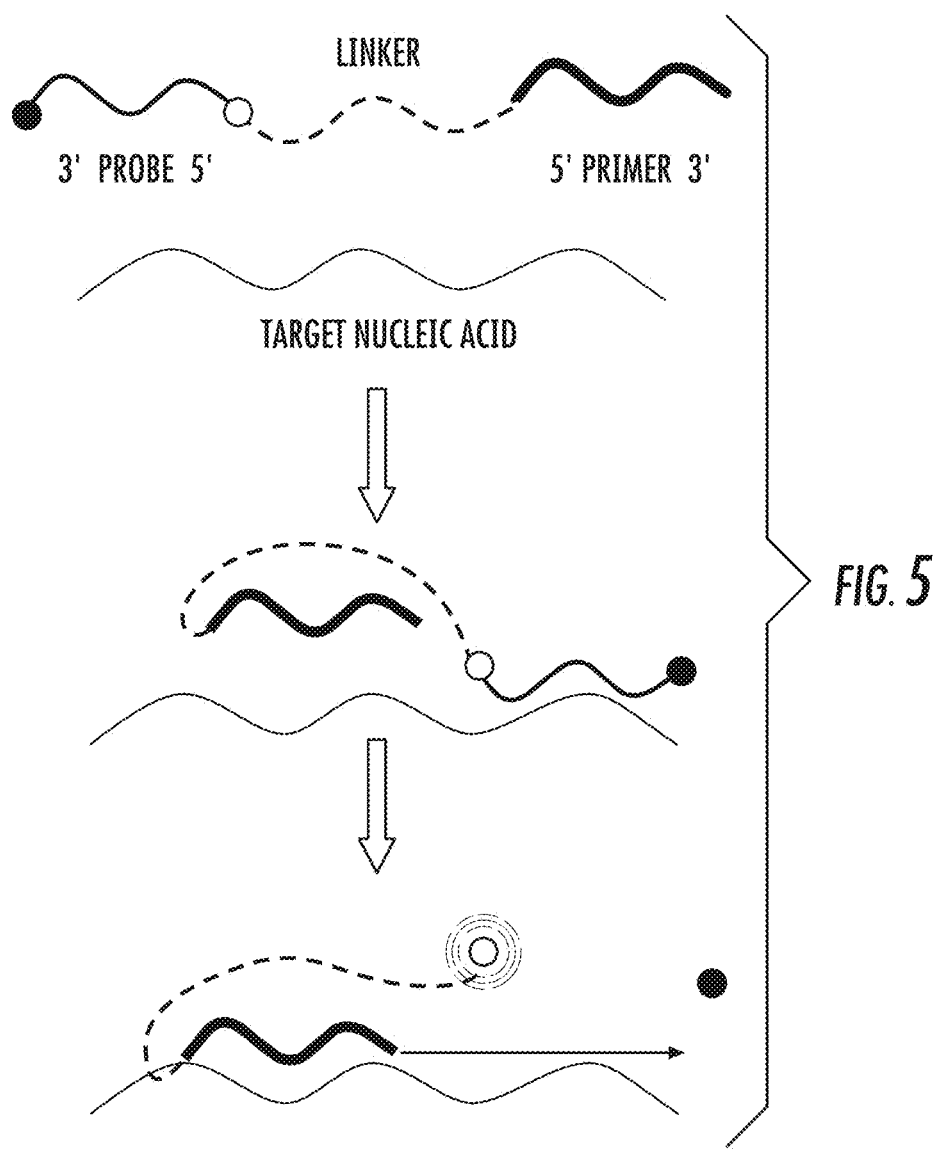

SEQUENCE LISTING

<160> NUMBER OF SEQ ID NOS: 67

<210> SEQ ID NO 1
<211> LENGTH: 10
<212> TYPE: DNA
<213> ORGANISM: Artificial Sequence
<220> FEATURE:
<223> OTHER INFORMATION: Synthetic Construct

<400> SEQUENCE: 1
acgcatcgct                                                          10

```
<210> SEQ ID NO 2
<211> LENGTH: 14
<212> TYPE: DNA
<213> ORGANISM: Artificial Sequence
<220> FEATURE:
<223> OTHER INFORMATION: Synthetic Construct

<400> SEQUENCE: 2
acggtgaact ctca                                                         14

<210> SEQ ID NO 3
<211> LENGTH: 10
<212> TYPE: DNA
<213> ORGANISM: Artificial Sequence
<220> FEATURE:
<223> OTHER INFORMATION: Synthetic Construct

<400> SEQUENCE: 3
acgcatcgct                                                              10

<210> SEQ ID NO 4
<211> LENGTH: 14
<212> TYPE: DNA
<213> ORGANISM: Artificial Sequence
<220> FEATURE:
<223> OTHER INFORMATION: Synthetic Construct

<400> SEQUENCE: 4
acggtgaact ctca                                                         14

<210> SEQ ID NO 5
<211> LENGTH: 10
<212> TYPE: DNA
<213> ORGANISM: Artificial Sequence
<220> FEATURE:
<223> OTHER INFORMATION: Synthetic Construct

<400> SEQUENCE: 5
acgcatcgct                                                              10

<210> SEQ ID NO 6
<211> LENGTH: 15
<212> TYPE: DNA
<213> ORGANISM: Artificial Sequence
<220> FEATURE:
<223> OTHER INFORMATION: Synthetic Construct

<400> SEQUENCE: 6
tctaacggtg aactc                                                        15

<210> SEQ ID NO 7
<211> LENGTH: 10
<212> TYPE: DNA
<213> ORGANISM: Artificial Sequence
<220> FEATURE:
<223> OTHER INFORMATION: Synthetic Construct

<400> SEQUENCE: 7
acgcatcgct                                                              10

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct
```

```
<400> SEQUENCE: 8
acggtgaact ctcattcca                                              19

<210> SEQ ID NO 9
<211> LENGTH: 10
<212> TYPE: DNA
<213> ORGANISM: Artificial Sequence
<220> FEATURE:
<223> OTHER INFORMATION: Synthetic Construct

<400> SEQUENCE: 9
acgcatcgct                                                        10

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct

<400> SEQUENCE: 10
acggtgaact ctcattccac cg                                          22

<210> SEQ ID NO 11
<211> LENGTH: 14
<212> TYPE: DNA
<213> ORGANISM: Artificial Sequence
<220> FEATURE:
<223> OTHER INFORMATION: Synthetic Construct

<400> SEQUENCE: 11
cgtccataca gtta                                                   14

<210> SEQ ID NO 12
<211> LENGTH: 15
<212> TYPE: DNA
<213> ORGANISM: Artificial Sequence
<220> FEATURE:
<223> OTHER INFORMATION: Synthetic Construct

<400> SEQUENCE: 12
agcaagtgga atgtt                                                  15

<210> SEQ ID NO 13
<211> LENGTH: 15
<212> TYPE: DNA
<213> ORGANISM: Artificial Sequence
<220> FEATURE:
<223> OTHER INFORMATION: Synthetic Construct

<400> SEQUENCE: 13
agcaagtgga atgtt                                                  15

<210> SEQ ID NO 14
<211> LENGTH: 14
<212> TYPE: DNA
<213> ORGANISM: Artificial Sequence
<220> FEATURE:
<223> OTHER INFORMATION: Synthetic Construct

<400> SEQUENCE: 14
cgtccataca gtta                                                   14
```

```
<210> SEQ ID NO 15
<211> LENGTH: 15
<212> TYPE: DNA
<213> ORGANISM: Artificial Sequence
<220> FEATURE:
<223> OTHER INFORMATION: Synthetic Construct

<400> SEQUENCE: 15
agcaagtgga atgtt                                                      15

<210> SEQ ID NO 16
<211> LENGTH: 14
<212> TYPE: DNA
<213> ORGANISM: Artificial Sequence
<220> FEATURE:
<223> OTHER INFORMATION: Synthetic Construct

<400> SEQUENCE: 16
cgtccataca gtta                                                       14

<210> SEQ ID NO 17
<211> LENGTH: 15
<212> TYPE: DNA
<213> ORGANISM: Artificial Sequence
<220> FEATURE:
<223> OTHER INFORMATION: Synthetic Construct

<400> SEQUENCE: 17
agcaagtgga atgtt                                                      15

<210> SEQ ID NO 18
<211> LENGTH: 14
<212> TYPE: DNA
<213> ORGANISM: Artificial Sequence
<220> FEATURE:
<223> OTHER INFORMATION: Synthetic Construct

<400> SEQUENCE: 18
cgtccataca gtta                                                       14

<210> SEQ ID NO 19
<211> LENGTH: 15
<212> TYPE: DNA
<213> ORGANISM: Artificial Sequence
<220> FEATURE:
<223> OTHER INFORMATION: Synthetic Construct

<400> SEQUENCE: 19
agcaagtgga atgtt                                                      15

<210> SEQ ID NO 20
<211> LENGTH: 14
<212> TYPE: DNA
<213> ORGANISM: Artificial Sequence
<220> FEATURE:
<223> OTHER INFORMATION: Synthetic Construct

<400> SEQUENCE: 20
cgtccataca gtta                                                       14

<210> SEQ ID NO 21
<211> LENGTH: 18
<212> TYPE: DNA
<213> ORGANISM: Artificial Sequence
<220> FEATURE:
<223> OTHER INFORMATION: Synthetic Construct
```

```
<400> SEQUENCE: 21
agcaagtgga atgttaga                                                     18

<210> SEQ ID NO 22
<211> LENGTH: 14
<212> TYPE: DNA
<213> ORGANISM: Artificial Sequence
<220> FEATURE:
<223> OTHER INFORMATION: Synthetic Construct

<400> SEQUENCE: 22
cgtccataca gtta                                                         14

<210> SEQ ID NO 23
<211> LENGTH: 15
<212> TYPE: DNA
<213> ORGANISM: Artificial Sequence
<220> FEATURE:
<223> OTHER INFORMATION: Synthetic Construct

<400> SEQUENCE: 23
agcaagtgga atgtt                                                        15

<210> SEQ ID NO 24
<211> LENGTH: 15
<212> TYPE: DNA
<213> ORGANISM: Artificial Sequence
<220> FEATURE:
<223> OTHER INFORMATION: Synthetic Construct

<400> SEQUENCE: 24
cgtccataca gttat                                                        15

<210> SEQ ID NO 25
<211> LENGTH: 22
<212> TYPE: DNA
<213> ORGANISM: Artificial Sequence
<220> FEATURE:
<223> OTHER INFORMATION: Synthetic Construct

<400> SEQUENCE: 25
tgtggccgag gactttgacg gc                                                22

<210> SEQ ID NO 26
<211> LENGTH: 12
<212> TYPE: DNA
<213> ORGANISM: Artificial Sequence
<220> FEATURE:
<223> OTHER INFORMATION: Synthetic Construct

<400> SEQUENCE: 26
ctggaacggt ga                                                           12

<210> SEQ ID NO 27
<211> LENGTH: 13
<212> TYPE: DNA
<213> ORGANISM: Artificial Sequence
<220> FEATURE:
<223> OTHER INFORMATION: Synthetic Construct

<400> SEQUENCE: 27
ggtgacagca gtc                                                          13
```

```
<210> SEQ ID NO 28
<211> LENGTH: 14
<212> TYPE: DNA
<213> ORGANISM: Artificial Sequence
<220> FEATURE:
<223> OTHER INFORMATION: Synthetic Construct

<400> SEQUENCE: 28
gtggctttta ggat                                                       14

<210> SEQ ID NO 29
<211> LENGTH: 13
<212> TYPE: DNA
<213> ORGANISM: Artificial Sequence
<220> FEATURE:
<223> OTHER INFORMATION: Synthetic Construct

<400> SEQUENCE: 29
gcaagggact tcc                                                        13

<210> SEQ ID NO 30
<211> LENGTH: 173
<212> TYPE: DNA
<213> ORGANISM: Artificial Sequence
<220> FEATURE:
<223> OTHER INFORMATION: Synthetic Construct

<400> SEQUENCE: 30
aggatttaaa aactggaacg gtgaaggtga cagcagtcgg ttggagcgag catcccccaa     60
agttcacaat gtggccgagg actttgattg cacattgttg ttttttttaat agtcattcca  120 aatatgagat gcgttgttac aggaagtccc ttgccatcct aaaagccacc cca          173

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct

<400> SEQUENCE: 31
cgcatcgctt ctaacggtga                                                 20

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
gaagcaaaca ctagcggtgg aa                                              22

<210> SEQ ID NO 33
<211> LENGTH: 44
<212> TYPE: DNA
<213> ORGANISM: Artificial Sequence
<220> FEATURE:
<223> OTHER INFORMATION: Synthetic Construct

<400> SEQUENCE: 33
actctcattc caatggaacc ttgttcaagt tcaaaccatt ggaa                      44
```

```
<210> SEQ ID NO 34
<211> LENGTH: 10
<212> TYPE: DNA
<213> ORGANISM: Artificial Sequence
<220> FEATURE:
<223> OTHER INFORMATION: Synthetic Construct

<400> SEQUENCE: 34
acgcatcgct                                                              10

<210> SEQ ID NO 35
<211> LENGTH: 14
<212> TYPE: DNA
<213> ORGANISM: Artificial Sequence
<220> FEATURE:
<223> OTHER INFORMATION: Synthetic Construct

<400> SEQUENCE: 35
acggtgaact ctca                                                         14

<210> SEQ ID NO 36
<211> LENGTH: 10
<212> TYPE: DNA
<213> ORGANISM: Artificial Sequence
<220> FEATURE:
<223> OTHER INFORMATION: Synthetic Construct

<400> SEQUENCE: 36
acgcatcgct                                                              10

<210> SEQ ID NO 37
<211> LENGTH: 18
<212> TYPE: DNA
<213> ORGANISM: Artificial Sequence
<220> FEATURE:
<223> OTHER INFORMATION: Synthetic Construct

<400> SEQUENCE: 37
cggtgaactc tcattcca                                                     18

<210> SEQ ID NO 38
<211> LENGTH: 10
<212> TYPE: DNA
<213> ORGANISM: Artificial Sequence
<220> FEATURE:
<223> OTHER INFORMATION: Synthetic Construct

<400> SEQUENCE: 38
acgcatcgct                                                              10

<210> SEQ ID NO 39
<211> LENGTH: 22
<212> TYPE: DNA
<213> ORGANISM: Artificial Sequence
<220> FEATURE:
<223> OTHER INFORMATION: Synthetic Construct

<400> SEQUENCE: 39
acggtgaact ctcattccac cg                                                22

<210> SEQ ID NO 40
<211> LENGTH: 24
<212> TYPE: DNA
<213> ORGANISM: Artificial Sequence
<220> FEATURE:
<223> OTHER INFORMATION: Synthetic Construct
```

```
<400> SEQUENCE: 40
acggtgaact ctcaacgcat cgct                                          24

<210> SEQ ID NO 41
<211> LENGTH: 15
<212> TYPE: DNA
<213> ORGANISM: Artificial Sequence
<220> FEATURE:
<223> OTHER INFORMATION: Synthetic Construct

<400> SEQUENCE: 41
agcaagtgga atgtt                                                    15

<210> SEQ ID NO 42
<211> LENGTH: 10
<212> TYPE: DNA
<213> ORGANISM: Artificial Sequence
<220> FEATURE:
<223> OTHER INFORMATION: Synthetic Construct

<400> SEQUENCE: 42
acgcatcgct                                                          10

<210> SEQ ID NO 43
<211> LENGTH: 14
<212> TYPE: DNA
<213> ORGANISM: Artificial Sequence
<220> FEATURE:
<223> OTHER INFORMATION: Synthetic Construct

<400> SEQUENCE: 43
cgtccataca gtta                                                     14

<210> SEQ ID NO 44
<211> LENGTH: 42
<212> TYPE: DNA
<213> ORGANISM: Artificial Sequence
<220> FEATURE:
<223> OTHER INFORMATION: Synthetic Construct

<400> SEQUENCE: 44
gaagcaaaca ctagcggtgg aatcaccgtt agaagcgatg cg                      42

<210> SEQ ID NO 45
<211> LENGTH: 24
<212> TYPE: DNA
<213> ORGANISM: Artificial Sequence
<220> FEATURE:
<223> OTHER INFORMATION: Synthetic Construct

<400> SEQUENCE: 45
cgtccataca gttaagcgat gcgt                                          24

<210> SEQ ID NO 46
<211> LENGTH: 9
<212> TYPE: DNA
<213> ORGANISM: Artificial Sequence
<220> FEATURE:
<223> OTHER INFORMATION: Synthetic Construct

<400> SEQUENCE: 46 actgtatgg                                                            9
```

```
<210> SEQ ID NO 47
<211> LENGTH: 7
<212> TYPE: DNA
<213> ORGANISM: Artificial Sequence
<220> FEATURE:
<223> OTHER INFORMATION: Synthetic Construct

<400> SEQUENCE: 47 atggacg                                                                    7

<210> SEQ ID NO 48
<211> LENGTH: 10
<212> TYPE: DNA
<213> ORGANISM: Artificial Sequence
<220> FEATURE:
<223> OTHER INFORMATION: Synthetic Construct

<400> SEQUENCE: 48
taactgtatg                                                                10

<210> SEQ ID NO 49
<211> LENGTH: 9
<212> TYPE: DNA
<213> ORGANISM: Artificial Sequence
<220> FEATURE:
<223> OTHER INFORMATION: Synthetic Construct

<400> SEQUENCE: 49 actgtatgg                                                                  9

<210> SEQ ID NO 50
<211> LENGTH: 160
<212> TYPE: DNA
<213> ORGANISM: Artificial Sequence
<220> FEATURE:
<223> OTHER INFORMATION: Synthetic Construct

<400> SEQUENCE: 50
ccagctcacg catcgcttct aacggtgaac tctcattcca atggaaccttt gttcaagttc         60 aaatagattg gtaaggtata gtgtttacta tcaaatgaaa caatgtgttc caccgctagt        120
gtttgctcta acattccact tgcttataac tgtatggacg                              160

<210> SEQ ID NO 51
<211> LENGTH: 22
<212> TYPE: DNA
<213> ORGANISM: Artificial Sequence
<220> FEATURE:
<223> OTHER INFORMATION: Synthetic Construct

<400> SEQUENCE: 51
cgccgcgatc aaggagttcg cg                                                  22

<210> SEQ ID NO 52
<211> LENGTH: 12
<212> TYPE: DNA
<213> ORGANISM: Artificial Sequence
<220> FEATURE:
<223> OTHER INFORMATION: Synthetic Construct

<400> SEQUENCE: 52
gaggcgatca ca                                                             12
```

```
<210> SEQ ID NO 53
<211> LENGTH: 13
<212> TYPE: DNA
<213> ORGANISM: Artificial Sequence
<220> FEATURE:
<223> OTHER INFORMATION: Synthetic Construct

<400> SEQUENCE: 53
cgcagacgtt gat                                                        13

<210> SEQ ID NO 54
<211> LENGTH: 29
<212> TYPE: DNA
<213> ORGANISM: Artificial Sequence
<220> FEATURE:
<223> OTHER INFORMATION: Synthetic Construct

<400> SEQUENCE: 54
tggaccatga attggctcag cgggttgtt                                       29

<210> SEQ ID NO 55
<211> LENGTH: 27
<212> TYPE: DNA
<213> ORGANISM: Artificial Sequence
<220> FEATURE:
<223> OTHER INFORMATION: Synthetic Construct

<400> SEQUENCE: 55
tggaccatga attggcagcg ggttgtt                                         27

<210> SEQ ID NO 56
<211> LENGTH: 31
<212> TYPE: DNA
<213> ORGANISM: Artificial Sequence
<220> FEATURE:
<223> OTHER INFORMATION: Synthetic Construct

<400> SEQUENCE: 56
catgaattgg ctcagctggg gttgttctgg a                                    31

<210> SEQ ID NO 57
<211> LENGTH: 32
<212> TYPE: DNA
<213> ORGANISM: Artificial Sequence
<220> FEATURE:
<223> OTHER INFORMATION: Synthetic Construct

<400> SEQUENCE: 57
catgaattgg ctcagctgcg ggttgttcta ga                                   32

<210> SEQ ID NO 58
<211> LENGTH: 26
<212> TYPE: DNA
<213> ORGANISM: Artificial Sequence
<220> FEATURE:
<223> OTHER INFORMATION: Synthetic Construct

<400> SEQUENCE: 58
tggaccatga attggagcgg gttgtt                                          26

<210> SEQ ID NO 59
<211> LENGTH: 26
<212> TYPE: DNA
<213> ORGANISM: Artificial Sequence
<220> FEATURE:
<223> OTHER INFORMATION: Synthetic Construct
```

```
<400> SEQUENCE: 59
tggaccatga attgcagcgg gttgtt                                        26

<210> SEQ ID NO 60
<211> LENGTH: 25
<212> TYPE: DNA
<213> ORGANISM: Artificial Sequence
<220> FEATURE:
<223> OTHER INFORMATION: Synthetic Construct

<400> SEQUENCE: 60
tggaccatga attcagcggg ttgtt                                         25

<210> SEQ ID NO 61
<211> LENGTH: 31
<212> TYPE: DNA
<213> ORGANISM: Artificial Sequence
<220> FEATURE:
<223> OTHER INFORMATION: Synthetic Construct

<400> SEQUENCE: 61
catgaattgg ctcagctggg gttgttctcg a                                  31

<210> SEQ ID NO 62
<211> LENGTH: 31
<212> TYPE: DNA
<213> ORGANISM: Artificial Sequence
<220> FEATURE:
<223> OTHER INFORMATION: Synthetic Construct

<400> SEQUENCE: 62
catgaattgg ctcagctggg gttcttctgg a                                  31

<210> SEQ ID NO 63
<211> LENGTH: 198
<212> TYPE: DNA
<213> ORGANISM: Artificial Sequence
<220> FEATURE:
<223> OTHER INFORMATION: Synthetic Construct

<400> SEQUENCE: 63
cgtggaggcg atcacaccgc agacgttgat caacatccgg ccggtggtcg ccgcgatcaa    60
ggagttcttc ggcaccagcc agctgagcca attcatggac cagaacaacc cgctgtcggg   120
gttgacccac aagcgccgac tgtcggcgct ggggcccggc ggtctgtcac gtgagcgtgc   180
cgggctggag gtccgcga                                                 198

<210> SEQ ID NO 64
<211> LENGTH: 198
<212> TYPE: DNA
<213> ORGANISM: Artificial Sequence
<220> FEATURE:
<223> OTHER INFORMATION: Synthetic Construct

<400> SEQUENCE: 64
cgtggaggcg atcacaccgc agacgttgat caacatccgg ccggtggtcg ccgcgatcaa    60
ggagttcttc ggcaccagcc agctgagcca attcatggtc cagaacaacc cgctgtcggg   120
gttgacccac aagcgccgac tgtcggcgct ggggcccggc ggtctgtcac gtgagcgtgc   180
cgggctggag gtccgcga                                                 198
```

```
<210> SEQ ID NO 65
<211> LENGTH: 9
<212> TYPE: DNA
<213> ORGANISM: Artificial Sequence
<220> FEATURE:
<223> OTHER INFORMATION: Synthetic Construct

<400> SEQUENCE: 65 actgtatgg                                                                 9

<210> SEQ ID NO 66
<211> LENGTH: 9
<212> TYPE: DNA
<213> ORGANISM: Artificial Sequence
<220> FEATURE:
<223> OTHER INFORMATION: Synthetic Construct

<400> SEQUENCE: 66 actgtatgg                                                                 9

<210> SEQ ID NO 67
<211> LENGTH: 14
<212> TYPE: DNA
<213> ORGANISM: Artificial Sequence
<220> FEATURE:
<223> OTHER INFORMATION: Synthetic Construct

<400> SEQUENCE: 67
cgtccataca gtta                                                          14
```

COOPERATIVE PRIMERS, PROBES, AND APPLICATIONS THEREOF

CROSS-REFERENCE TO RELATED APPLICATIONS

This application is a continuation application of U.S. application Ser. No. 13/944,192, filed Jul. 17, 2013, which claims benefit of U.S. Provisional Application No. 61/672,329, filed Jul. 17, 2012, and 61/732,537, filed Dec. 3, 2012, each of which are hereby incorporated herein by reference in their entirety.

FIELD OF THE INVENTION

The disclosed invention is generally in the field of nucleic acid amplification in its entirety.

BACKGROUND OF THE INVENTION

Nucleic acid testing often requires amplification of nucleic acids to achieve a sufficient concentration and/or purity to undergo subsequent testing. Sometimes amplification of nucleic acids is used as a surrogate in detection of non-nucleic acids, such as proteins. The majority of nucleic acid amplification/extension reactions depend on the presence of a primer comprised of modified or natural nucleic acids at the 3' end which allow extension in the presence of a polymerase.

A universal problem with such amplification reactions is the presence of primer-dimers. Primer-dimers are formed when primers extend each other rather than the target nucleic acid. Primer-dimers use up primers, resulting in the presence of impurities in the reaction. Even worse, primer-dimers can use up enough primers to cause false negatives in some cases. Or, if interacting with a probe, primer-dimers can cause false positives.

A variety of hot starts have been developed to deal with the issue of primer-dimers including suspending the polymerase in a wax material, inhibiting the polymerase with antibodies, chemically modifying the polymerase, sequestering primers, and a variety of other methods. The problem with all of these methods is that they are only effective prior to the first round of amplification/extension. Any primer-dimers that form thereafter are amplified at an exponential rate.

Other methods of dealing with primer-dimers include methods such as nested PCR. However, this requires two separate reactions and increases the chances of contamination.

Many amplification/extension reactions are also coupled with a detection probe. The principles often revolve around a labeled linear probe, such as Taqman or a labeled hairpin probe such as Molecular Beacons. Some methods achieve incredible specificity through the use of cooperatively linking two probes, such as Tentacle Probes. However, each of these probe based methods is limited in detecting mutants in a high background of wild type. While they can achieve all or nothing detection of single nucleotide polymorphisms and other mutations, they can only pick out about one mutant in a background of 10 to 20 wild type sequences. This is because the primers amplify both the wild type and the mutant and are depleted without being able to detect both. Methods like ARMS can be combined with the probe detection technologies to overcome this problem to an extent, but cannot be effectively multiplexed for real-time detection when more than one mutation occurs in the same general region.

Several primers have been developed which include a detection mechanism, such as Amplifluor primers, Rapid Detex primers and Scorpion primers. The first two are especially prone to false positives from primer-dimer problems because they are not sequence specific. The latter is a self-probing primer, where the probe binds to the primer extension product rather than the nucleic acid template. Because it has a sequence specific probe, it is less likely to result in false positives, but is still subject to primer-dimer associated problems.

BRIEF SUMMARY OF THE INVENTION

Disclosed herein is a cooperative nucleic acid molecule comprising: a) a first nucleic acid sequence, wherein the first nucleic acid sequence is substantially complementary to a first region of a target nucleic acid, and wherein the first nucleic acid sequence is extendable on the 3' end; b) a second nucleic acid sequence, wherein the second nucleic acid sequence is substantially complementary to a second region of the target nucleic acid; wherein the first and second nucleic acid sequences are attached to each other; and wherein the second nucleic acid sequence hybridizes to the target nucleic acid sequence downstream from the 3' end of the first nucleic acid sequence.

Further disclosed is a method for amplifying a target nucleic acid, the method comprising: a) providing a cooperative nucleic acid molecule as disclosed herein; b) providing a target nucleic acid; and c) amplifying the target nucleic acid under appropriate conditions for amplification; thereby amplifying the target nucleic acid.

Also disclosed is a method for detecting a nucleic acid in a sample, the method comprising a) providing a cooperative nucleic acid molecule as disclosed herein, wherein the cooperative nucleic acid comprises a detectable label; b) providing a target nucleic acid; and c) detecting the target nucleic acid; thereby detecting the target nucleic acid.

BRIEF DESCRIPTION OF THE DRAWINGS

FIG. 5 shows a preferred embodiment for detection of nucleic acid extension using a cooperative primer linked to a dual labeled probe. The probe binds to the target nucleic acid, and the hybridized probe holds the primer in close proximity to the target. The primer extends, cleaving the probe, causing an increase in fluorescence.

FIG. 6A shows normal primers have some primer-dimer (P-D) formation even when no P-D are spiked in, however, still 25 have amplification of 60 starting copies of Malaria DNA. When 600 P-D are spiked in, Malaria amplification products are eclipsed and only P-D are amplified. In contrast, FIG. 6B shows Cooperative Primers have no primer-dimer amplification, even when up to 600,000 P-D are spiked in. P-D do not interfere with cooperative primer amplification of the target nucleic acid.

DETAILED DESCRIPTION OF THE INVENTION

Figure 1:
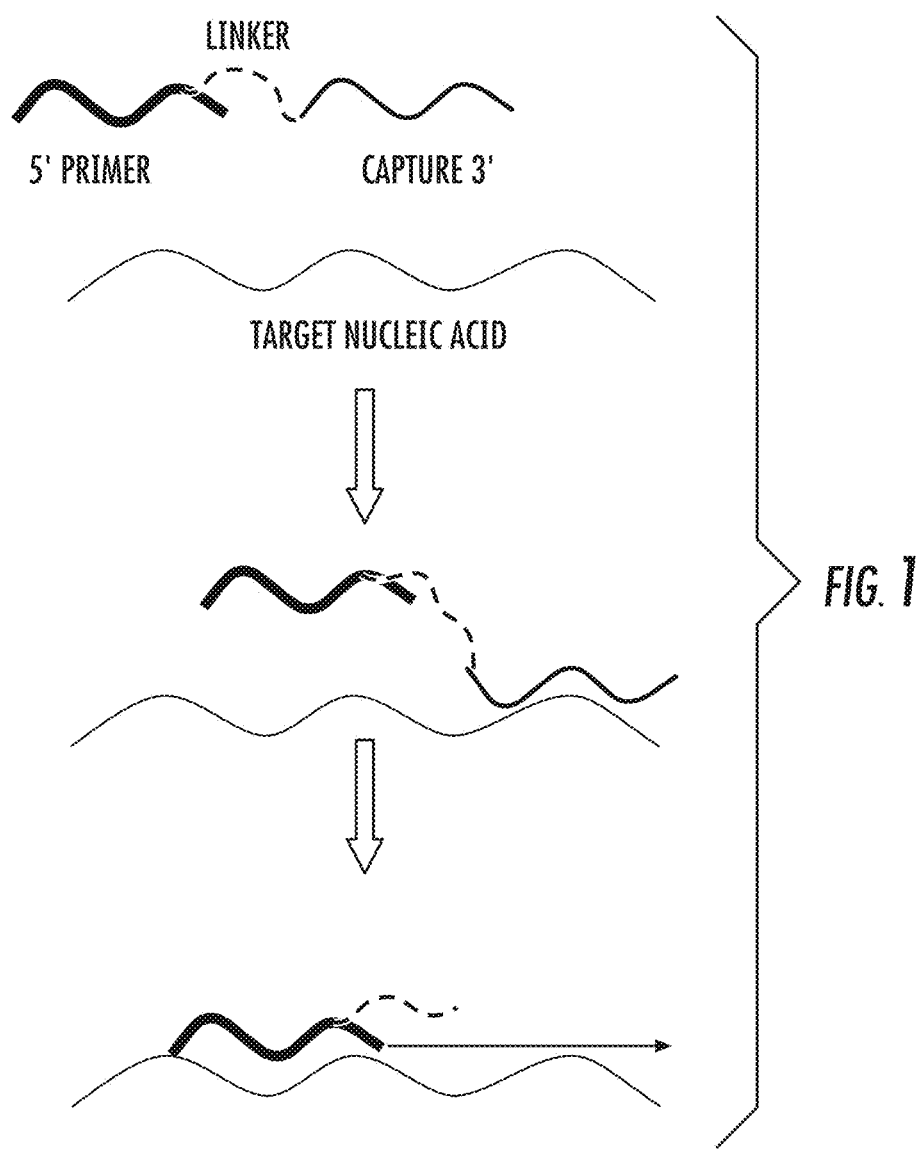
FIG. 1 shows an embodiment of cooperative primers that has a linker internal to the primer attached to the 5' end of the capture sequence. The capture sequence binds to the target nucleic acid, and the hybridized capture sequence holds the primer in close proximity to the target. The primer then extends, cleaving the capture sequence.

The disclosed method makes use of certain materials and procedures which allow amplification of nucleic acid sequences and whole genomes or other highly complex nucleic acid samples. These materials and procedures are described in detail below.

Definitions

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used herein, "nucleic acid sequence" refers to the order or sequence of nucleotides along a strand of nucleic acids. In some cases, the order of these nucleotides may determine the order of the amino acids along a corresponding polypeptide chain. The nucleic acid sequence thus codes for the amino acid sequence. The nucleic acid sequence may be single-stranded or double-stranded, as specified, or contain portions of both double-stranded and single-stranded sequences. The nucleic acid sequence may be composed of DNA, both genomic and cDNA, RNA, or a hybrid, where the sequence comprises any combination of deoxyribo- and ribo-nucleotides, and any combination of bases, including uracil (U), adenine (A), thymine (T), cytosine (C), guanine (G), inosine, xathanine hypoxathanine, isocytosine, isoguanine, etc. It may include modified bases, including locked nucleic acids, peptide nucleic acids and others known to those skilled in the art.

An "oligonucleotide" is a polymer comprising two or more nucleotides. The polymer can additionally comprise non-nucleotide elements such as labels, quenchers, blocking groups, or the like. The nucleotides of the oligonucleotide can be natural or non-natural and can be unsubstituted, unmodified, substituted or modified. The nucleotides can be linked by phosphodiester bonds, or by phosphorothioate linkages, methylphosphonate linkages, boranophosphate linkages, or the like.

A "peptide nucleic acid" (PNA) is a polymer comprising two or more peptide nucleic acid monomers. The polymer can additionally comprise elements such as labels, quenchers, blocking groups, or the like. The monomers of the PNA can be unsubstituted, unmodified, substituted or modified.

By "cooperative nucleic acid" is meant a nucleic acid sequence which incorporates minimally a first nucleic acid sequence and a second nucleic acid sequence, wherein the second nucleic acid sequence hybridizes to the target nucleic acid downstream of the 3' end of the first nucleic acid sequence. The 3' end of the nucleic acid can be extendable, as discussed elsewhere herein. In one example, the first nucleic acid is a primer, and the second nucleic acid is a capture sequence. The first and second nucleic acid sequences can be separated by a linker, for example.

A "primer" is a nucleic acid that contains a sequence complementary to a region of a template nucleic acid strand and that primes the synthesis of a strand complementary to the template (or a portion thereof). Primers are typically, but need not be, relatively short, chemically synthesized oligonucleotides (typically, deoxyribonucleotides). In an amplification, e.g., a PCR amplification, a pair of primers typically define the 5' ends of the two complementary strands of the nucleic acid target that is amplified. By "cooperative primer," or first nucleic acid sequence, is meant a primer attached via a linker to a second nucleic acid sequence, also referred to as a capture sequence. The second nucleic acid sequence, or capture sequence, can hybridize to the template nucleic acid downstream of the 3' end of the primer, or first nucleic acid sequence. By "normal primer" is meant a primer which does not have a capture sequence, or second nucleic acid sequence, attached to it via a linker.

By "capture sequence," which is also referred to herein as a "second nucleic acid sequence" is meant a sequence which hybridizes to the target nucleic acid and allows the first nucleic acid sequence, or primer sequence, to be in close proximity to the target region of the target nucleic acid.

"Downstream" is relative to the action of the polymerase during nucleic acid synthesis or extension. For example, when the Taq polymerase extends a primer, it adds bases to the 3' end of the primer and will move towards a sequence that is "downstream from the 3' end of the primer."

A "target region" is a region of a target nucleic acid that is to be amplified, detected or both.

The "Tm" (melting temperature) of a nucleic acid duplex under specified conditions is the temperature at which half of the nucleic acid sequences are disassociated and half are associated. As used herein, "isolated Tm" refers to the individual melting temperature of either the first or second nucleic acid sequence in the cooperative nucleic acid when not in the cooperative pair. "Effective Tm" refers to the resulting melting temperature of either the first or second nucleic acid when linked together.

The term "linker" means the composition joining the first and second nucleic acids to each other. The linker comprises at least one non-extendable moiety, but may also comprise extendable nucleic acids, and can be any length. The linker may be connected to the 3' end, the 5' end, or can be connected one or more bases from the end ("the middle") of both the first and second nucleic acid sequences. The connection can be covalent, hydrogen bonding, ionic interactions, hydrophobic interactions, and the like. The term "non-extendable" has reference to the inability of the native Taq polymerase to recognize a moiety and thereby continue nucleic acid synthesis. A variety of natural and modified nucleic acid bases are recognized by the polymerase and are "extendable." Examples of non-extendable moieties include among others, fluorophores, quenchers, polyethylene glycol, polypropylene glycol, polyethylene, polypropylene, polyamides, polyesters and others known to those skilled in the art. In some cases, even a nucleic acid base with reverse orientation (e.g. 5' ACGT 3' 3'A 5' 5' AAGT 3') or otherwise rendered such that the Taq polymerase could not extend through it could be considered "non-extendable." The term "non-nucleic acid linker" as used herein refers to a reactive chemical group that is capable of covalently attaching a first nucleic acid to a second nucleic acid, or more specifically, the primer to the capture sequence. Suitable flexible linkers are typically linear molecules in a chain of at least one or two atoms, more typically an organic polymer chain of 1 to 12 carbon atoms (and/or other backbone atoms) in length. Exemplary flexible linkers include polyethylene glycol, polypropylene glycol, polyethylene, polypropylene, polyamides, polyesters and the like.

As used herein, "complementary" or "complementarity" refers to the ability of a nucleotide in a polynucleotide molecule to form a base pair with another nucleotide in a second polynucleotide molecule. For example, the sequence 5'-A-C-T-3' is complementary to the sequence 3'-T-G-A-5'. Complementarity may be partial, in which only some of the nucleotides match according to base pairing, or complete, where all the nucleotides match according to base pairing. For purposes of the present invention "substantially complementary" refers to 90% or greater identity over the length of the target base pair region. The complementarity can also be 50, 60, 70, 75, 80, 85, 90, 91, 92, 93, 94, 95, 96, 97, 98, 99, or 100% complementary, or any amount below or in between these amounts.

As used herein, "amplify, amplifying, amplifies, amplified, amplification" refers to the creation of one or more identical or complementary copies of the target DNA. The copies may be single stranded or double stranded. Amplification can be part of a number of processes such as extension of a primer, reverse transcription, polymerase chain reaction, nucleic acid sequencing, rolling circle amplification and the like.

As used herein, "purified" refers to a polynucleotide, for example a target nucleic acid sequence, that has been separated from cellular debris, for example, high molecular weight DNA, RNA and protein. This would include an isolated RNA sample that would be separated from cellular debris, including DNA. It can also mean non-native, or non-naturally occurring nucleic acid.

As used herein, "protein," "peptide," and "polypeptide" are used interchangeably to denote an amino acid polymer or a set of two or more interacting or bound amino acid polymers.

As used herein, "stringency" refers to the conditions, i.e., temperature, ionic strength, solvents, and the like, under which hybridization between polynucleotides occurs. Hybridization being the process that occurs between the primer and template DNA during the annealing step of the amplification process.

A variety of additional terms are defined or otherwise characterized herein.

Materials and Methods

The present invention relates to cooperative nucleic acids, such as primers and probes. A cooperative nucleic acid comprises an oligonucleotide primer linked to a second oligonucleotide which is complementary to a region of the template downstream from the 3' end of the primer (as seen in FIG. 1 for example). This second oligonucleotide serves as a capture sequence. In some embodiments, this allows primers with low melting temperatures ("Tm") to hybridize efficiently to the target.

The capture sequence holds the primer in close proximity to the template allowing extension/amplification to occur in spite of the low Tm. However, nonspecific sequences that do not have a complementary sequence to the capture sequence, such as primer-dimers, are not extended efficiently. Because the capture sequence uniquely hybridizes downstream from the 3' end of the primer, the specificity of amplification is achieved in every cycle. This is in contrast with conventional hot start methods, whose specificity wears off after the first cycle.

This is also in contrast with concepts such as the dual specificity primer (US Patent Publication 20120135473, herein incorporated by reference in its entirety for its teaching concerning dual specificity primers). The dual specificity primer has a capture sequence linked to a short primer via Inosine residues where the capture sequence hybridizes to the target on the 5' side of the primer. The result is that the dual specificity primer is highly specific in the first round of amplification. However, if the dual specificity primers amplify each other, the polymerase extends all the way through to the 5' end, creating a high Tm primer-dimer that will be propagated in every round thereafter. This is in contrast to the cooperative nucleic acid where the capture sequence hybridizes to the target on the 3' side of the primer, preventing it from being incorporated into the primer-dimer in the order necessary to allow for propagation of the primer-dimer.

The cooperative nucleic acids and methods of using them are also different than "padlock probes" (Nilsson et al. 1994: "Padlock probes: circularizing oligonucleotides for localized DNA detection". Science 265 (5181): 2085-2088), Molecular Inversion Probes (MIPs) (Hardenbol et al 2003: "Multiplexed genotyping with sequence-tagged molecular inversion probes". Nat Biotechnol 21 (6): 673-678) and Connector Inversion Probes (CIPs) (Akhras et al. 2007: Hall, Neil. ed. "Connector inversion probe technology: a powerful one-primer multiplex DNA amplification system for numerous scientific applications". PLoS ONE 2 (9): e195). For example, the probes disclosed herein can have a linker with at least one non-extendable moiety. Furthermore, the molecule disclosed herein is a primer, whereas the "padlock probes" are ligated, and the non-ligated padlock probes are digested or otherwise removed prior to amplification and cannot be used as primers.

Padlock probes are single stranded DNA molecules with two 20-nucleotide long segments complementary to the target connected by a 40-nucleotide long linker sequence.

When the target complementary regions are hybridized to the DNA target, the padlock probes also become circularized. However, unlike MIP, padlock probes are designed such that the target complementary regions span the entire target region upon hybridization, leaving no gaps. Thus, padlock probes are only useful for detecting DNA molecules with known sequences.

Molecular Inversion probes were developed to perform SNP genotyping, which are modified padlock probes such that when the probe is hybridized to the genomic target, there is a gap at the SNP position. Gap filling using a nucleotide that is complementary to the nucleotide at the SNP location determines the identity of the polymorphism. This design brings numerous benefits over the more traditional padlock probe technique. Using multiple padlock probes specific to a plausible SNP requires careful balancing of the concentration of these allele specific probes to ensure SNP counts at a given locus are properly normalized.

Connector Inversion Probes make use of a modified design of MIP by extending the gap delimited by the hybridized probe ends and named the design Connector Inversion Probe (CIP). The gap corresponds to the genomic region of interest to be captured (e.g. exons). Gap filling reaction is achieved with DNA polymerase, using all four nucleotides. Identification of the captured regions can then be done by sequencing them using locus-specific primers that map to one of the target complementary ends of the probes.

A "primer dimer" (PD) is a potential by-product in PCR. As its name implies, a PD consists of primer molecules that have attached (hybridized) to each other because of strings of complementary bases in the primers or through other nonspecific interactions. As a result, the DNA polymerase amplifies the PD, leading to competition for PCR reagents, thus potentially inhibiting amplification of the DNA sequence targeted for PCR amplification. In real-time PCR, PDs may interfere with accurate quantification through signal dampening, false negatives, false positives and the like.

The present invention also relates to cooperatively linked nucleic acids that also comprise a probe. This modified primer/probe is similar to the cooperative nucleic acid, but with the addition of one or more detectable labels to either the capture sequence or the primer, turning it into a probe. Because extension of the cooperative primer/probe is detectable, it can be useful in a variety of applications including multiplexing applications that require differentiation of SNP's using an ARMS based approach. In some embodiments, both the primer and the probe are designed with Tm's below the melting temperature which is used in the amplification reaction, so that the primer will not amplify without the probe binding and the probe will not have a signal without the primer binding. This creates two points of specificity in the same primer/probe combination.

The cooperative nucleic acids, such as primers and probes, of this invention are useful in a variety of primer extension/amplification reactions known to those skilled in the art, including, but not limited to the polymerase chain reaction, rolling circle amplification, nucleic acid sequencing and others. The cooperative primers and probes of this invention can also be used in applications that have post extension/amplification steps, such as hybridization to an array. Because the cooperative primers/probes in this invention substantially reduce primer-dimers, they are of particular use in multiplexed and highly multiplexed reactions.

The use of a cooperative nucleic acid can decrease the amount of primer-dimer present by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent compared to the amount of primer-dimer present when a normal primer (a non-cooperative nucleic acid) is used.

Therefore, disclosed herein is a cooperative nucleic acid molecule comprising: a) a first nucleic acid sequence, wherein the first nucleic acid sequence is substantially complementary to a first region of a target nucleic acid, and wherein the first nucleic acid sequence is extendable on the 3' end; b) a second nucleic acid sequence, wherein the second nucleic acid sequence is substantially complementary to a second region of the target nucleic acid; wherein the first and second nucleic acid sequences are attached to each other; and wherein the second nucleic acid sequence hybridizes to the target nucleic acid sequence downstream from the 3' end of the first nucleic acid sequence; and wherein the effective melting temperature (Tm) of the first nucleic acid molecule is increased by at least 1° C. as compared to the isolated Tm of the first nucleic acid sequence without the second nucleic acid sequence attached to it.

The cooperative nucleic acid may be linear or circularized.

By "extendable on the 3' end" is meant that the first nucleic acid is free on this end to be amplified, or extended. This is meant to include heat activatable primers such as those described by Lebedev et al, among other technologies.

The first nucleic acid sequence is a primer, and the second nucleic acid sequence is alternatively referred to as a "capture nucleic acid sequence." Either the first or the second sequence may have a detectable label, or a third sequence may have a detectable label. The first and second nucleic acid sequences can be attached via a linker, which can be a non-nucleic acid sequence. In one example, the linker can attach the 5' end of the first nucleic acid sequence to the 3' end of the second nucleic acid sequence. This can be seen, for instance, in FIG. 2. Alternatively, the the first nucleic acid sequence is inverted such that the 5' end of the first nucleic acid sequence is attached to the 5' end of the second nucleic acid sequence. This can be seen, for instance, in FIG. 3. In yet another example, the 5' end of the second nucleic acid sequence can be linked to the first nucleic acid sequence in the middle of the sequence, as seen in FIG. 1. It is noted that by "middle of the sequence" is meant that the linker is not joined to the first nucleic acid sequence at either the 5' end or the 3' end of the nucleic acid, but rather is attached to a nucleotide internal to the nucleotides on the 5' and 3' ends.

In one example, the cooperative nucleic acid comprises 75, 70, 65, 60, 55, 50, 45, 40, 35, 30, 25, 20, 15, 10, or less continuous nucleotides in the same orientation. In other words, this is the number of nucleotides that are part of a single, unbroken nucleic acid sequence and oriented in the same 5' to 3' direction, or the 3' to 5' direction. By way of example, if the linker is a nucleic acid sequence, it can include the linker, if the nucleotides in the linker are in the same orientation as either the first or second nucleic acid sequence to which it is directly connected.

The linker can be made of nucleic acids, non-nucleic acids, or some combination of both. If the linker is made of nucleic acids, it can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 or more nucleotides in length, or any number in between. Types of linkers are discussed elsewhere herein. The linker can be any length, and can be longer or shorter than the combined length of the first and second nucleic acid sequences, longer or shorter than just the first nucleic acid sequence, or longer or shorter than the second nucleic acid sequence.

Furthermore, there can be a space on the target nucleic acid where the first nucleic acid sequence and the second nucleic acid sequence hybridize. In other words, there are two distinct regions on the target nucleic acid, one which hybridizes with the first nucleic acid sequence, and the other which hybridizes to the second nucleic acid sequence. The distance between the first and second regions on the target can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 or more nucleotides in length.

Also disclosed herein is a kit comprising the cooperative nucleic acid molecules disclosed herein together with instructions for their use. In some embodiments, additional cooperative nucleic acid molecules are provided in the kit. In still others, reagents for performing the extension are included, such as polymerase, dNTP's, buffers and the like. In some embodiments, positive and negative controls may be included. In such embodiments, the reagents may all be packaged separately or combined in a single tube or container.

Further disclosed is a method for amplifying a target nucleic acid, the method comprising: a) providing a cooperative nucleic acid molecule as disclosed herein; b) providing a target nucleic acid; and c) amplifying the target nucleic acid under appropriate conditions for amplification; wherein the effective Tm of the first nucleic acid molecule is increased by at least 1° C. as compared to the isolated Tm of the first nucleic acid sequence without the second nucleic acid sequence attached to it; thereby amplifying the target nucleic acid.

Methods of amplification are disclosed elsewhere herein. More than one cooperative nucleic acid molecule can be provided, and they can have the same or different sequences. For example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 or more nucleic acid molecules of different sequences can be provided.

Primer Design

In some embodiments, the isolated melting temperature "Tm" of the primer, also referred to herein as the first nucleic acid sequence, is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more degrees below the reaction temperature used during the annealing phase, of PCR, or the extension phase of reactions with no annealing phase. Therefore, the melting temperature of the primer sequence can be between about 1° C. and 40° C., between about 3° C. and 20° C., between about 5° C. and 15° C. below the reaction temperature used in the PCR reaction. In a preferred embodiment, the isolated Tm is between about 7° C. and 12° C. below the reaction temperature. This provides for less than 50%, and more preferably less than 20% of the template to be hybridized to an isolated primer.

One of skill in the art can design primers with a given melting temperature based on many factors, such as length, and with increasing GC content. A simple formula for calculation of the (Tm) is:

$$Tm = 4(G+C) + 2(A+T)° C.$$

Furthermore, one of skill in the art will appreciate that the actual Tm is influenced by the concentration of $Mg^{2+}$, $K^+$, and cosolvents. There are numerous computer programs to assist in primer design.

To achieve the desired melting temperatures, the first nucleic acid sequence, or the primer, can be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 bases in length. For example, the primers can be between about 5 and 26, between about 7 and 22, between about 9 and 17 bases in length depending on GC content.

Any desired number of primers of different nucleotide sequence can be used, but use of one or a few primers is preferred. The amplification reaction can be performed with, for example, one, two, three, four, five, six, seven, eight, nine, ten, eleven, twelve, thirteen, fourteen, fifteen, sixteen, or seventeen primers. More primers can be used. There is no fundamental upper limit to the number of primers that can be used. However, the use of fewer primers is preferred. When multiple primers are used, the primers should each have a different specific nucleotide sequence.

The amplification reaction can be performed with a single primer and, for example, with no additional primers, with 1 additional primer, with 2 additional primers, with 3 additional primers, with 4 additional primers, with 5 additional primers, with 6 additional primers, with 7 additional primers, with 8 additional primers, with 9 additional primers, with 10 additional primers, with 11 additional primers, with 12 additional primers, with 13 additional primers, with 14 additional primers, with 15 additional primers, with 16 additional primers, with 17 additional primers, with 18 additional primers, with 19 additional primers, with 20 additional primers, with 21 additional primers, with 22 additional primers, with 23 additional primers, with 24 additional primers, with 25 additional primers, with 26 additional primers, with 27 additional primers, with 28 additional primers, with 29 additional primers, with 30 additional primers, with 31 additional primers, with 32 additional primers, with 33 additional primers, with 34 additional primers, with 35 additional primers, with 36 additional primers, with 37 additional primers, with 38 additional primers, with 39 additional primers, with 40 additional primers, with 41 additional primers, with 42 additional primers, with 43 additional primers, with 44 additional primers, with 45 additional primers, with 46 additional primers, with 47 additional primers, with 48 additional primers, with 49 additional primers, with 50 additional primers, with 51 additional primers, with 52 additional primers, with 53 additional primers, with 54 additional primers, with 55 additional primers, with 56 additional primers, with 57 additional primers, with 58 additional primers, with 59 additional primers, with 60 additional primers, with 61 additional primers, with 62 additional primers, with 63 additional primers, with 64 additional primers, with 65 additional primers, with 66 additional primers, with 67 additional primers, with 68 additional primers, with 69 additional primers, with 70 additional primers, with 71 additional primers, with 72 additional primers, with 73 additional primers, with 74 additional primers, with 75 additional primers, with 76 additional primers, with 77 additional primers, with 78 additional primers, with 79 additional primers, with 80 additional primers, with 81 additional primers, with 82 additional primers, with 83 additional primers, with 84 additional primers, with 85 additional primers, with 86 additional primers, with 87 additional primers, with 88 additional primers, with 89 additional primers, with 90 additional primers, with 91 additional primers, with 92 additional primers, with 93 additional primers, with 94 additional primers, with 95 additional primers, with 96 additional primers, with 97 additional primers, with 98 additional primers, with 99 additional primers, with 100 additional primers, with 110 additional primers, with 120 additional primers, with 130 additional primers, with 140 additional primers, with 150 additional primers, with 160 additional primers, with 170 additional primers, with 180 additional primers, with 190 additional primers, with 200 additional primers, with 210 additional primers, with 220 additional primers, with 230 additional primers, with 240 additional primers, with 250 additional primers, with 260 additional primers, with 270 additional primers, with 280 additional primers, with 290 additional primers, with 300 additional primers, with 310 additional primers, with 320 additional primers, with 330 additional primers, with 340 additional primers, with 350 additional primers, with 360 additional primers, with 370 additional primers, with 380 additional primers, with 390 additional primers, with 400 additional primers, with 410 additional primers, with 420 additional primers, with 430 additional primers, with 440 additional primers, with 450 additional primers, with 460 additional primers, with 470 additional primers, with 480 additional primers, with 490 additional primers, with 500 additional primers, with 550 additional primers, with 600 additional primers, with 650 additional primers, with 700 additional primers, with 750 additional primers, with 800 additional primers, with 850 additional primers, with 900 additional primers, with 950 additional primers, with 1,000 additional primers, with 1,100 additional primers, with 1,200 additional primers, with 1,300 additional primers, with 1,400 additional primers, with 1,500 additional primers, with 1,600 additional primers, with 1,700 additional primers, with 1,800 additional primers, with 1,900 additional primers, with 2,000 additional primers, with 2,100 additional primers, with 2,200 additional primers, with 2,300 additional primers, with 2,400 additional primers, with 2,500 additional primers, with 2,600 additional primers, with 2,700 additional primers, with 2,800 additional primers, with 2,900 additional primers, with 3,000 additional primers, with 3,500 additional primers, or with 4,000 additional primers.

The amplification reaction can be performed with a single primer and, for example, with no additional primers, with fewer than 2 additional primers, with fewer than 3 additional primers, with fewer than 4 additional primers, with fewer than 5 additional primers, with fewer than 6 additional primers, with fewer than 7 additional primers, with fewer than 8 additional primers, with fewer than 9 additional primers, with fewer than 10 additional primers, with fewer than 11 additional primers, with fewer than 12 additional primers, with fewer than 13 additional primers, with fewer than 14 additional primers, with fewer than 15 additional primers, with fewer than 16 additional primers, with fewer than 17 additional primers, with fewer than 18 additional primers, with fewer than 19 additional primers, with fewer than 20 additional primers, with fewer than 21 additional primers, with fewer than 22 additional primers, with fewer than 23 additional primers, with fewer than 24 additional primers, with fewer than 25 additional primers, with fewer than 26 additional primers, with fewer than 27 additional primers, with fewer than 28 additional primers, with fewer than 29 additional primers, with fewer than 30 additional primers, with fewer than 31 additional primers, with fewer than 32 additional primers, with fewer than 33 additional primers, with fewer than 34 additional primers, with fewer than 35 additional primers, with fewer than 36 additional primers, with fewer than 37 additional primers, with fewer than 38 additional primers, with fewer than 39 additional primers, with fewer than 40 additional primers, with fewer than 41 additional primers, with fewer than 42 additional primers, with fewer than 43 additional primers, with fewer than 44 additional primers, with fewer than 45 additional primers, with fewer than 46 additional primers, with fewer than 47 additional primers, with fewer than 48 additional primers, with fewer than 49 additional primers, with fewer than 50 additional primers, with fewer than 51 additional primers, with fewer than 52 additional primers, with fewer than 53 additional primers, with fewer than 54 additional primers, with fewer than 55 additional primers, with fewer than 56 additional primers, with fewer than 57 additional primers, with fewer than 58 additional primers, with fewer than 59 additional primers, with fewer than 60 additional primers, with fewer than 61 additional primers, with fewer than 62 additional primers, with fewer than 63 additional primers, with fewer than 64 additional primers, with fewer than 65 additional primers, with fewer than 66 additional primers, with fewer than 67 additional primers, with fewer than 68 additional primers, with fewer than 69 additional primers, with fewer than 70 additional primers, with fewer than 71 additional primers, with fewer than 72 additional primers, with fewer than 73 additional primers, with fewer than 74 additional primers, with fewer than 75 additional primers, with fewer than 76 additional primers, with fewer than 77 additional primers, with fewer than 78 additional primers, with fewer than 79 additional primers, with fewer than 80 additional primers, with fewer than 81 additional primers, with fewer than 82 additional primers, with fewer than 83 additional primers, with fewer than 84 additional primers, with fewer than 85 additional primers, with fewer than 86 additional primers, with fewer than 87 additional primers, with fewer than 88 additional primers, with fewer than 89 additional primers, with fewer than 90 additional primers, with fewer than 91 additional primers, with fewer than 92 additional primers, with fewer than 93 additional primers, with fewer than 94 additional primers, with fewer than 95 additional primers, with fewer than 96 additional primers, with fewer than 97 additional primers, with fewer than 98 additional primers, with fewer than 99 additional primers, with fewer than 100 additional primers, with fewer than 110 additional primers, with fewer than 120 additional primers, with fewer than 130 additional primers, with fewer than 140 additional primers, with fewer than 150 additional primers, with fewer than 160 additional primers, with fewer than 170 additional primers, with fewer than 180 additional primers, with fewer than 190 additional primers, with fewer than 200 additional primers, with fewer than 210 additional primers, with fewer than 220 additional primers, with fewer than 230 additional primers, with fewer than 240 additional primers, with fewer than 250 additional primers, with fewer than 260 additional primers, with fewer than 270 additional primers, with fewer than 280 additional primers, with fewer than 290 additional primers, with fewer than 300 additional primers, with fewer than 310 additional primers, with fewer than 320 additional primers, with fewer than 330 additional primers, with fewer than 340 additional primers, with fewer than 350 additional primers, with fewer than 360 additional primers, with fewer than 370 additional primers, with fewer than 380 additional primers, with fewer than 390 additional primers, with fewer than 400 additional primers, with fewer than 410 additional primers, with fewer than 420 additional primers, with fewer than 430 additional primers, with fewer than 440 additional primers, with fewer than 450 additional primers, with fewer than 460 additional primers, with fewer than 470 additional primers, with fewer than 480 additional primers, with fewer than 490 additional primers, with fewer than 500 additional primers, with fewer than 550 additional primers, with fewer than 600 additional primers, with fewer than 650 additional primers, with fewer than 700 additional primers, with fewer than 750 additional primers, with fewer than 800 additional primers, with fewer than 850 additional primers, with fewer than 900 additional primers, with fewer than 950 additional primers, with fewer than 1,000 additional primers, with fewer than 1,100 additional primers, with fewer than 1,200 additional primers, with fewer than 1,300 additional primers, with fewer than fewer than 1,400 additional primers, with fewer than 1,500 additional primers, with fewer than 1,600 additional primers, with fewer than 1,700 additional primers, with fewer than 1,800 additional primers, with fewer than 1,900 additional primers, with fewer than 2,000 additional primers, with fewer than 2,100 additional primers, with fewer than 2,200 additional primers, with fewer than 2,300 additional primers, with fewer than 2,400 additional primers, with fewer than 2,500 additional primers, with fewer than 2,600 additional primers, with fewer than 2,700 additional primers, with fewer than 2,800 additional primers, with fewer than 2,900 additional primers, with fewer than 3,000 additional primers, with fewer than 3,500 additional primers, or with fewer than 4,000 additional primers.

The amplification reaction can be performed, for example, with fewer than 2 primers, with fewer than 3 primers, with fewer than 4 primers, with fewer than 5 primers, with fewer than 6 primers, with fewer than 7 primers, with fewer than 8 primers, with fewer than 9 primers, with fewer than 10 primers, with fewer than 11 primers, with fewer than 12 primers, with fewer than 13 primers, with fewer than 14 primers, with fewer than 15 primers, with fewer than 16 primers, with fewer than 17 primers, with fewer than 18 primers, with fewer than 19 primers, with fewer than 20 primers, with fewer than 21 primers, with fewer than 22 primers, with fewer than 23 primers, with fewer than 24 primers, with fewer than 25 primers, with fewer than 26 primers, with fewer than 27 primers, with fewer than 28 primers, with fewer than 29 primers, with fewer than 30 primers, with fewer than 31 primers, with fewer than 32 primers, with fewer than 33 primers, with fewer than 34 primers, with fewer than 35 primers, with fewer than 36 primers, with fewer than 37 primers, with fewer than 38 primers, with fewer than 39 primers, with fewer than 40 primers, with fewer than 41 primers, with fewer than 42 primers, with fewer than 43 primers, with fewer than 44 primers, with fewer than 45 primers, with fewer than 46 primers, with fewer than 47 primers, with fewer than 48 primers, with fewer than 49 primers, with fewer than 50 primers, with fewer than 51 primers, with fewer than 52 primers, with fewer than 53 primers, with fewer than 54 primers, with fewer than 55 primers, with fewer than 56 primers, with fewer than 57 primers, with fewer than 58 primers, with fewer than 59 primers, with fewer than 60 primers, with fewer than 61 primers, with fewer than 62 primers, with fewer than 63 primers, with fewer than 64 primers, with fewer than 65 primers, with fewer than 66 primers, with fewer than 67 primers, with fewer than 68 primers, with fewer than 69 primers, with fewer than 70 primers, with fewer than 71 primers, with fewer than 72 primers, with fewer than 73 primers, with fewer than 74 primers, with fewer than 75 primers, with fewer than 76 primers, with fewer than 77 primers, with fewer than 78 primers, with fewer than 79 primers, with fewer than 80 primers, with fewer than 81 primers, with fewer than 82 primers, with fewer than 83 primers, with fewer than 84 primers, with fewer than 85 primers, with fewer than 86 primers, with fewer than 87 primers, with fewer than 88 primers, with fewer than 89 primers, with fewer than 90 primers, with fewer than 91 primers, with fewer than 92 primers, with fewer than 93 primers, with fewer than 94 primers, with fewer than 95 primers, with fewer than 96 primers, with fewer than 97 primers, with fewer than 98 primers, with fewer than 99 primers, with fewer than 100 primers, with fewer than 110 primers, with fewer than 120 primers, with fewer than 130 primers, with fewer than 140 primers, with fewer than 150 primers, with fewer than 160 primers, with fewer than 170 primers, with fewer than 180 primers, with fewer than 190 primers, with fewer than 200 primers, with fewer than 210 primers, with fewer than 220 primers, with fewer than 230 primers, with fewer than 240 primers, with fewer than 250 primers, with fewer than 260 primers, with fewer than 270 primers, with fewer than 280 primers, with fewer than 290 primers, with fewer than 300 primers, with fewer than 310 primers, with fewer than 320 primers, with fewer than 330 primers, with fewer than 340 primers, with fewer than 350 primers, with fewer than 360 primers, with fewer than 370 primers, with fewer than 380 primers, with fewer than 390 primers, with fewer than 400 primers, with fewer than 410 primers, with fewer than 420 primers, with fewer than 430 primers, with fewer than 440 primers, with fewer than 450 primers, with fewer than 460 primers, with fewer than 470 primers, with fewer than 480 primers, with fewer than 490 primers, with fewer than 500 primers, with fewer than 550 primers, with fewer than 600 primers, with fewer than 650 primers, with fewer than 700 primers, with fewer than 750 primers, with fewer than 800 primers, with fewer than 850 primers, with fewer than 900 primers, with fewer than 950 primers, with fewer than 1,000 primers, with fewer than 1,100 primers, with fewer than 1,200 primers, with fewer than 1,300 primers, with fewer than fewer than 1,400 primers, with fewer than 1,500 primers, with fewer than 1,600 primers, with fewer than 1,700 primers, with fewer than 1,800 primers, with fewer than 1,900 primers, with fewer than 2,000 primers, with fewer than 2,100 primers, with fewer than 2,200 primers, with fewer than 2,300 primers, with fewer than 2,400 primers, with fewer than 2,500 primers, with fewer than 2,600 primers, with fewer than 2,700 primers, with fewer than 2,800 primers, with fewer than 2,900 primers, with fewer than 3,000 primers, with fewer than 3,500 primers, or with fewer than 4,000 primers.

The disclosed primers can have one or more modified nucleotides. Such primers are referred to herein as modified primers. Chimeric primers can also be used. Chimeric primers are primers having at least two types of nucleotides, such as both deoxyribonucleotides and ribonucleotides, ribonucleotides and modified nucleotides, two or more types of modified nucleotides, deoxyribonucleotides and two or more different types of modified nucleotides, ribonucleotides and two or more different types of modified nucleotides, or deoxyribonucleotides, ribonucleotides and two or more different types of modified nucleotides. One form of chimeric primer is peptide nucleic acid/nucleic acid primers. For example, 5'-PNA-DNA-3' or 5'-PNA-RNA-3' primers may be used for more efficient strand invasion and polymerization invasion. Other forms of chimeric primers are, for example, 5'-(2'-O-Methyl) RNA-RNA-3' or 5'-(2'-O-Methyl) RNA-DNA-3'.

Many modified nucleotides (nucleotide analogs) are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and 0-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. A primer having one or more universal bases is not considered to be a primer having a specific sequence.

Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[(CH$_2$)$_n$ O]$_m$ CH$_3$, —O(CH$_2$)$_n$ OCH$_3$, —O(CH$_2$)$_n$ NH$_2$, —O(CH$_2$)$_n$ CH$_3$, —O(CH$_2$)$_n$ —ONH$_2$, and —O(CH$_2$)$_n$ON [(CH$_2$)$_n$ CH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate nucleic acid molecules.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science 254:1497-1500 (1991)).

Primers can be comprised of nucleotides and can be made up of different types of nucleotides or the same type of nucleotides. For example, one or more of the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. The nucleotides can be comprised of bases (that is, the base portion of the nucleotide) and can (and normally will) comprise different types of bases.

Capture Sequence Design

The capture sequence, also referred to herein as the "second nucleic acid sequence," is complementary to the template such that it hybridizes to the target nucleic acid molecule downstream from the 3' end of the primer. In some embodiments, resistance to mutations in the target nucleic acid is desired and the capture sequence is designed with a melting temperature greater than the reaction temperature. In these embodiments, the capture sequence is designed with an isolated Tm of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more degrees above the reaction temperature. For example, the capture, or second, sequence is between about 0° C. and 40° C., between about 5° C. and 30° C., between about 7° C. and 25° C. above the reaction temperature. In some embodiments, the predicted melting temperature of the capture sequence is also made for expected mutants. In these embodiments, the isolated Tm of the capture sequence to the expected mutants is between about 1, 2, 3, 4, 5, 6, 7, 8, 9, 10, 11, 12, 13, 14, 15 16, 17, 18, 19, 20, or more degrees C. below the reaction temperature, or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 or more degrees C. above the reaction temperature. For example, it can be 10° C. below the reaction temperature and 30° C. above the reaction temperature, between about 3° C. below the reaction temperature and about 10° C. above the reaction temperature.

To achieve these melting temperatures, the capture sequence length can be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 or more bases in length. For example, it can be between about 20 and about 50, between about 22 and about 40, between about 23 and about 37 bases.

In some embodiments, an even higher resistance to mutations in the target sequence is desired. In these embodiments, in addition to a capture sequence with an isolated Tm of between about 0° C. and 40° C. above the reaction temperature, the cooperative primer is designed with an isolated Tm of between about 7° C. below and about 20° C. above, between about 5° C. below and about 10° C. above, between about 3° C. below and about 3° C. above the reaction temperature. The cooperative interaction between the primer and the capture sequence will result in an even greater effective Tm for the cooperative primer, rendering it almost impervious to mutations in the sequence. By comparison, a normal primer might have to be an additional 5 to 30 bases in length to have an equivalent resistance to mutations in the target sequence, and consequently, would be much more susceptible to primer-dimer formation.

In other embodiments, a higher resistance to primer-dimers is preferred and the melting temperature of the isolated capture, or second, nucleic acid sequence is designed to be less than the reaction temperature. For example, the capture, or second, nucleic acid sequence is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more degrees below the reaction temperature, or annealing phase, of PCR. In preferred embodiments, the Tm of the isolated capture, or second nucleic acid, sequence is between about 0° C. and 12° C., between about 1° C. and 8° C., between about 2° C. and 5° C. below the reaction temperature. To achieve these low melting temperatures, the capture sequence length can be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more bases in length. For example, the capture, or second nucleic acid sequence, can be between about 5 and 30, between about 8 and 25, and between about 10 and 22 bases.

In some embodiments, the capture sequence binds and releases the target sequence rapidly such that the polymerase can extend underneath the capture sequence, leaving the capture sequence intact. In some embodiments, this is enhanced using a cooperative primer with the linker attached to the 5' end of the capture sequence. In a preferred embodiment, the polymerase is capable of cleaving the capture sequence during extension. In a preferred embodiment, this is enhanced using a cooperative primer with the linker attached to the 3' end of the capture sequence.

Linker

The number of bases between the 3' end of the first nucleic acid, or primer, sequence and the 5' end of the second nucleic acid, or capture sequence hybridization locations in the template is important. In some embodiments, the number of bases between the primer and the capture sequence is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. For example, they can be between about 0 and 30, between about 0 and 20, between about 0 and 10 bases.

The more bases that are between the two sites, the longer the linker needs to be if cleavage of the capture sequence is desired. The longer the linker, the more entropy that enters into the system, which lowers the effect of cooperative binding. This is expressed in the following equation:

$$K_{eff} = K_{primer} + K_{capture} + L_C K_{primer} K_{capture}$$

Where Keff is the effective or cooperative equilibrium constant, Kprimer is the equilibrium constant of the primer in isolation, Kcapture is the equilibrium constant of the capture sequence in equilibrium and Lc is the local concentration defined as:

$$L_c = \frac{\left(\frac{1}{6.022E23}\right)}{\frac{4}{3}\pi r^3}$$

Where r is the linker length in decimeters. This provides the effective local concentration in molarity due to the cooperative interaction between the primer and the probe. Accordingly, linker length directly determines the cooperative contribution ($L_c K_{primer} K_{capture}$) to the effective equilibrium constant.

$K_{primer}$ and $K_{capture}$ can be calculated by obtaining the enthalpy and entropy values for the primer and the capture sequences using nearest neighbor or other calculations known to those skilled in the art.

The total amount of template bound by the primer can be calculated as follows:

$$\frac{T_{primer}}{T_o} = \frac{(K_{primer} + L_C K_{primer} K_{capture})P_o}{1 + (K_{primer} + K_{capture} + L_c K_{primer} K_{capture})P_o}$$

Where Tprimer is the template bound by primer, $T_o$ is the total amount of template and $P_o$ is the starting cooperative primer concentration. It can be seen that the cooperative effect is greatest when $L_c K_{primer} K_{capture}$ is much greater than $K_{primer}$. For this to occur the linker length should be as short as possible.

While the math shows that the linker length should be as short as possible, there are several limitations to how short the linker can actually be. When the capture sequence and the probe bind to the template, they form rigid double helices. The linker length must be sufficient to accommodate this structure.

Figure 2:
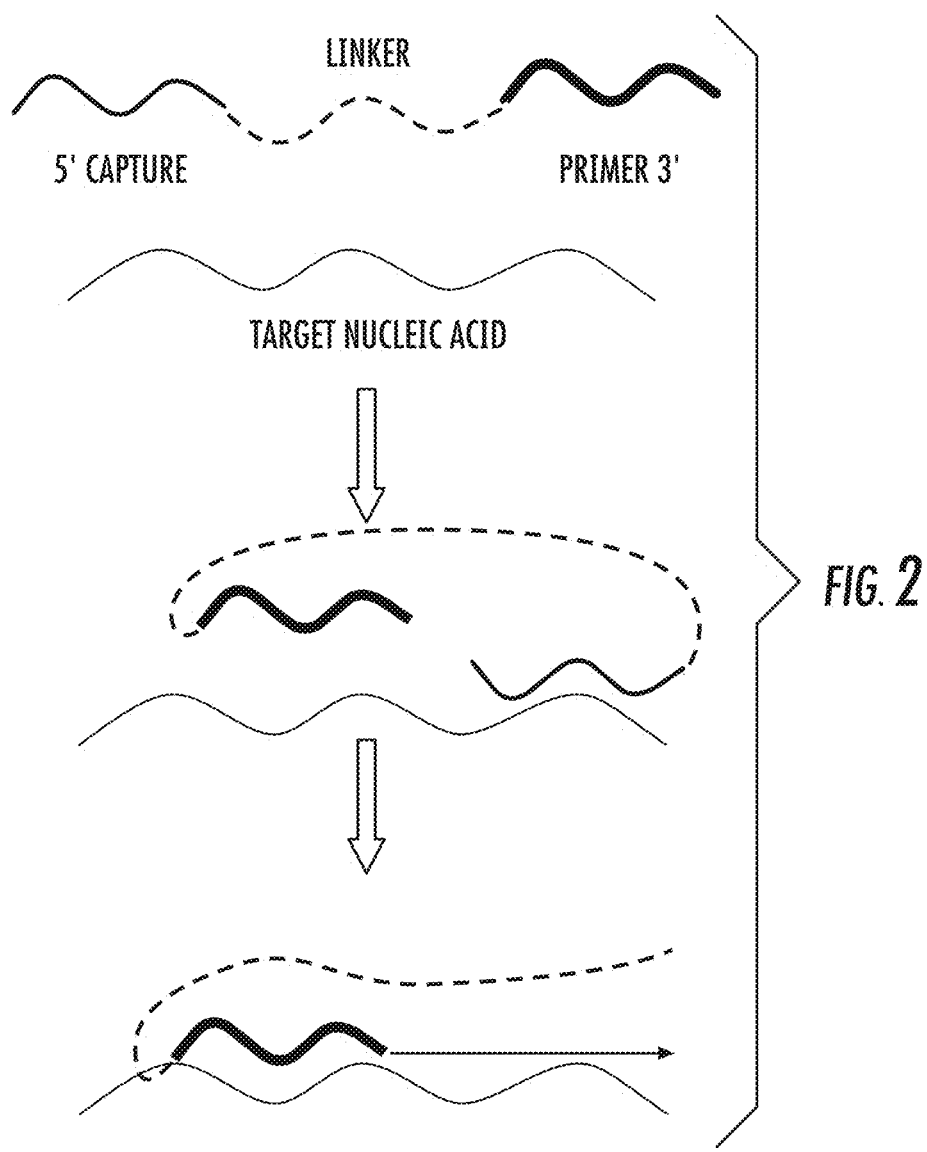
FIG. 2 shows another embodiment of cooperative primers that has a linker attaching the 5' end of the primer to the 3' end of the capture sequence. The capture sequence binds to the target nucleic acid. The hybridized capture sequence holds the primer in close proximity to the target. The primer then extends, cleaving the capture sequence.
Figure 3:
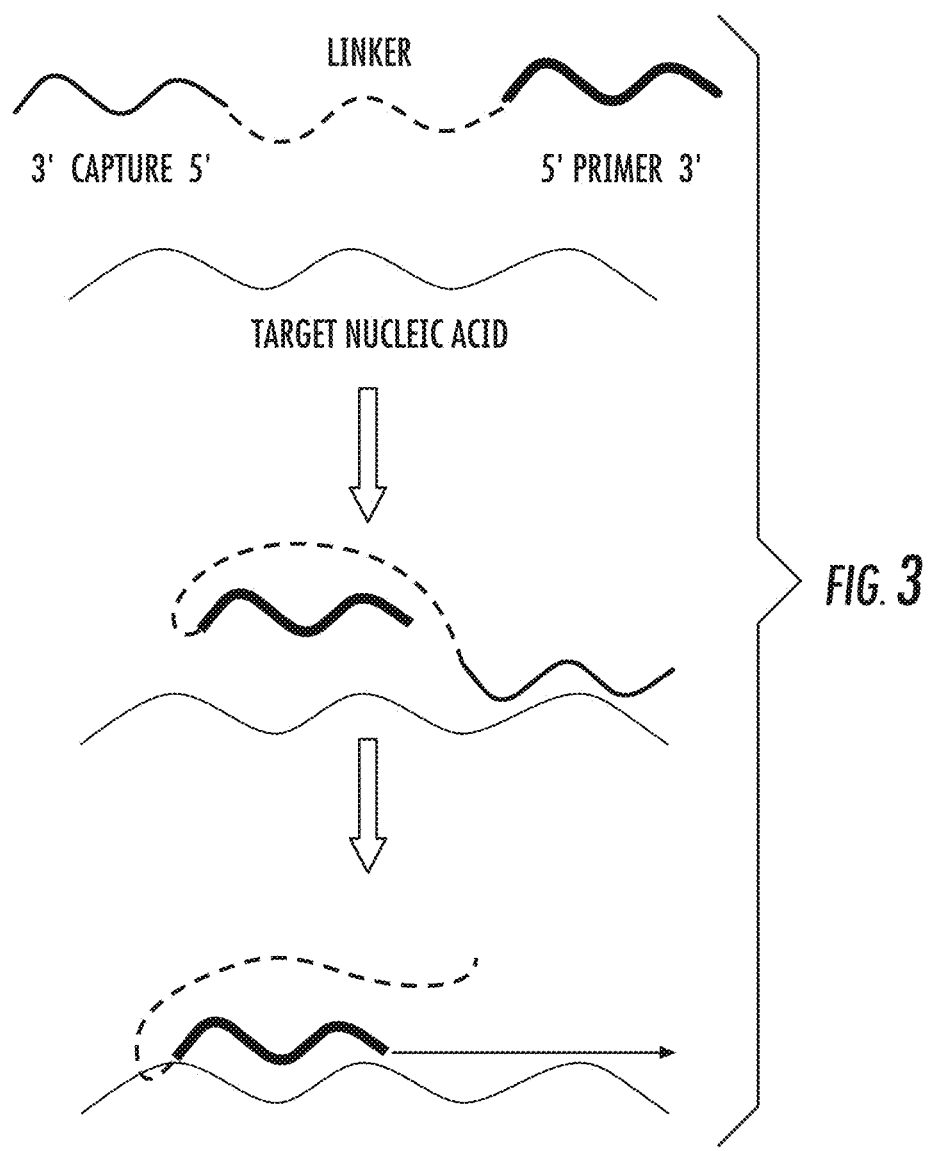
FIG. 3 shows a preferred embodiment of a cooperative primer with the 5' end of the capture sequence linked to the 5' end of the primer. The capture sequence binds to the target nucleic acid. The hybridized capture sequence holds the primer in close proximity to the target. The primer then extends, cleaving the capture sequence.

In some embodiments, the linker attaches the 5' end of the primer to the 3' end of the capture sequence (FIG. 2). In this embodiment, the linker is larger than the combined length of the primer and capture sequences. In a preferred embodiment where the linker attaches to the 3' end of the capture sequence, the linker comprises 6 hexaethylene glycols. In another embodiment, the primer is inverted such that the 5' end of the primer is attached to the 5' end of the capture sequence (FIG. 3). In this embodiment, the linker is longer than the primer. In a preferred embodiment where the linker attaches to the 5' end of the capture sequence, the linker comprises 3 hexaethylene glycols. In yet another embodiment, the 3' end of the capture sequence is linked to the middle of the primer (FIG. 1). In this instance, the linker may be shorter than the length of the primer.

A variety of linker types and compositions are known to those skilled in the art. Examples include, but are not limited to, polyethylene glycol and carbon linkers. Linkers can be attached through a variety of methods, including but not limited to, covalent bonds, ionic bonds, hydrogen bonding, polar association, magnetic association, and van der wals association. A preferred method is covalent bonding through standard DNA synthesis methods.

The length of polyethylene glycol linkers is about 0.34 nm per monomer. In some embodiments, the length of the polyethylene glycol linker is between about 1 and 90, between about 2 and 50, between about 3 and 30 monomers (between about 1 and 10 nm fully extended).

Using the Capture Sequence as a Probe

In some embodiments, it is preferable to have the capture sequence also serve as a probe. In some embodiments, this is done through the addition of one or more labels to the capture sequence. In a preferred embodiment, the labels include a FRET pair.

Figure 4:
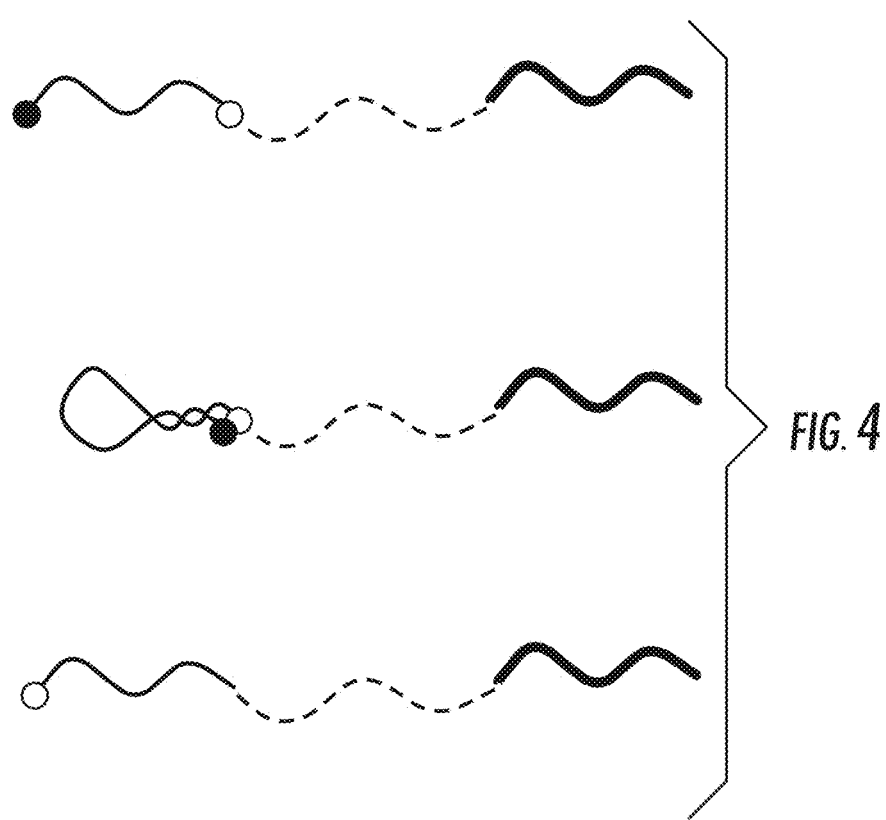
FIG. 4 shows examples of probes that can be linked to the primer include, but are not limited to, dual labeled probes, hairpin probes and single label probes.
Figures 6A, 6B:
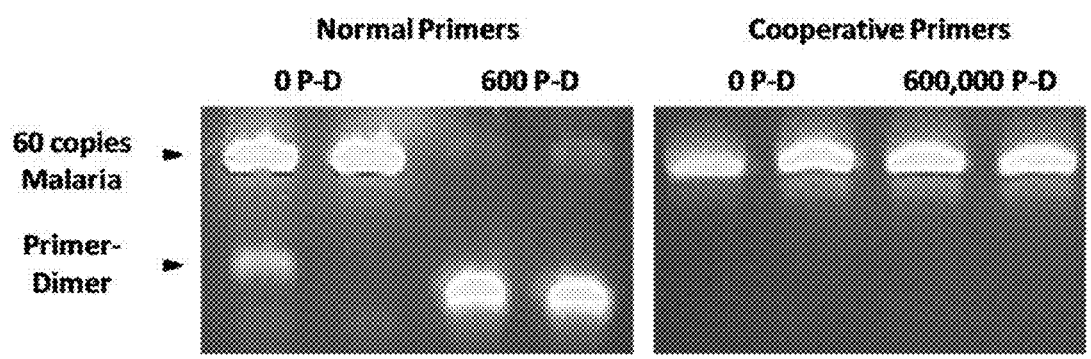
FIG. 6A-B shows gel of Cooperative Primers and Normal Primers.

Various nucleic acid probe constructs are known to those skilled in the art. These include, but are not limited to, dual labeled probes, hairpin probes, and single label probes (see FIG. 4).

In some embodiments, a low background signal is desired for high signal to noise ratios. In some embodiments, a hairpin probe is used to provide increased contact quenching to assist in providing high signal to noise.

In other embodiments, a shorter probe is desired to minimize primer-probe dimers. In some embodiments requiring a shorter probe, a dual labeled probe is used. In embodiments that require an even greater emphasis on the reduction of spurious extension products, the melting temperature of the isolated probe target complex is less than the reaction temperature.

A variety of methods for detecting signal from labeled probes are known to those skilled in the art. In some embodiments a polymerase is used that cleaves the probe, releasing a label that changes the signal. In other embodiments, a polymerase is used that does not cleave the probe. Rather the signal is modified by the hybridization of the probe to the template.

Using a Primer with a Built in Detection Mechanism

Figure 7:
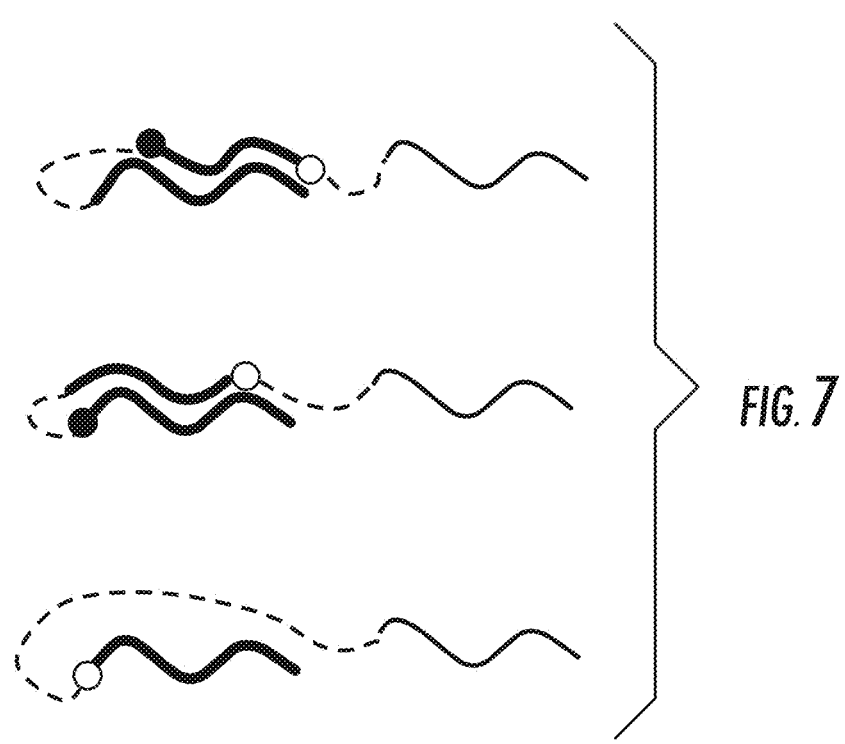
FIG. 7 shows some examples of primers with built in detection mechanisms that can be used in cooperative primers.

In some embodiments, the primer has a built in detection mechanism. In some embodiments the detection mechanism includes one or more detectable labels. In a preferred embodiment, the detection mechanism includes a FRET pair. Examples of primers with built in detection mechanisms include, but are not limited to, Amplifluor primers, Rapid Detex primers, and others known to those skilled in the art. An example of this is seen in FIG. 7.

Cooperative nucleic acids with built in detection mechanisms can be more useful to assay designers than non-cooperative nucleic acids (normal primers) with built in detection mechanisms. Without being limited by theory, this is because cooperative nucleic acids are less prone to generate signal from nonspecific products, such as primer-dimers.

In some embodiments, a nucleic acid binding dye, such as SYBR Green, is used to monitor the progress of the amplification reaction.

Fluorescent change probes and fluorescent change primers refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos, fluorescent water-soluble conjugated polymers, PNA probes and QPNA probes.

Fluorescent change probes and primers can be classified according to their structure and/or function. Fluorescent change probes include hairpin quenched probes, cleavage quenched probes, cleavage activated probes, and fluorescent activated probes. Fluorescent change primers include stem quenched primers and hairpin quenched primers. The use of several types of fluorescent change probes and primers are reviewed in Schweitzer and Kingsmore, Curr. Opin. Biotech. 12:21-27 (2001). Hall et al., Proc. Natl. Acad. Sci. USA 97:8272-8277 (2000), describe the use of fluorescent change probes with Invader assays.

Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during amplification), the quenching moiety is no longer in proximity to the fluorescent label and fluorescence increases. TaqMan probes (Holland et al., Proc. Natl. Acad. Sci. USA 88:7276-7280 (1991)) are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity. Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends a the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes.

Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. In the disclosed method, stem quenched primers are used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers (Nazerenko et al., Nucleic Acids Res. 25:2516-2521 (1997)) and scorpion primers (Thelwell et al., Nucleic Acids Res. 28(19):3752-3761 (2000)).

Cleavage activated primers are similar to cleavage activated probes except that they are primers that are incorporated into replicated strands and are then subsequently cleaved. Little et al., Clin. Chem. 45:777-784 (1999), describe the use of cleavage activated primers.

Multiplexing with ARMS

In some embodiments, detection of multiple polymorphisms, insertions, deletions or other mutations is desired. In some embodiments, the primer is designed such that the base on the 3' end is over the mutation. In some embodiments, additional intentional polymorphisms are designed into the primer. In one embodiment, the presence of a probe attached to the primer allows for allele specific real-time detection of multiple polymorphisms in the same location.

Mutation Differentiation with the Probe

In some embodiments the differentiation of polymorphisms is accomplished using the capture sequence attached to the primer. In some embodiments the capture sequence has additional mutations intentionally added to improve differentiation. In some embodiments, the capture sequence will not bind when a polymorphism is present, preventing efficient amplification round after around. In some embodiments where the capture sequence has a detectable label, even if some amplification does occur, the capture sequence does not bind sufficiently to generate a detectable signal.

RNA and Other Reactions

In some embodiments, a polymerase other than a DNA polymerase is used. A variety of polymerases and enzymes capable of adding one or more bases to a nucleic acid template are known to those skilled in the art. In some embodiments, reverse transcription is desired. In some embodiments, the probe has a sufficiently low melting temperature that the polymerase can extend underneath it. In other embodiments, an increase in the temperature after a time for initial polymerization removes the capture sequence from the template, allowing the polymerase to extend. In other embodiments, additional primer sequences are used that do not have a capture sequence, allowing the polymerase to make copies in an uninhibited fashion at lower reaction temperatures.

Target Nucleic Acid Molecules

Nucleic acid molecules, which are the object of amplification, can be any nucleic acid from any source. In general, the disclosed method is performed using a nucleic acid sample that contains (or is suspected of containing) nucleic acid molecules to be amplified.

A nucleic acid sample can be any nucleic acid sample of interest. The source, identity, and preparation of many such nucleic acid samples are known. It is preferred that nucleic acid samples known or identified for use in amplification or detection methods be used for the method described herein. The nucleic acid sample can be, for example, a nucleic acid sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful nucleic acid samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, a crude cell lysate samples, forensic samples, archeological samples, infection samples, nosocomial infection samples, production samples, drug preparation samples, biological molecule production samples, protein preparation samples, lipid preparation samples, and/or carbohydrate preparation samples.

For whole genome amplification, preferred nucleic acid samples are nucleic acid samples from a single cell. The nucleic acid samples for use in the disclosed method are preferably nucleic acid molecules and samples that are complex and non-repetitive. Where the nucleic acid sample is a genomic nucleic acid sample, the genome can be the genome from any organism of interest. For example, the genome can be a viral genome, a bacterial genome, a eubacterial genome, an archae bacterial genome, a fungal genome, a microbial genome, a eukaryotic genome, a plant genome, an animal genome, a vertebrate genome, an invertebrate genome, an insect genome, a mammalian genome, or a human genome. The target genome is preferably pure or substantially pure, but this is not required. For example, an genomic sample from an animal source may include nucleic acid from contaminating or infecting organisms.

The nucleic acid sample can be, or can be derived from, for example, one or more whole genomes from the same or different organisms, tissues, cells or a combination; one or more partial genomes from the same or different organisms, tissues, cells or a combination; one or more whole chromosomes from the same or different organisms, tissues, cells or a combination; one or more partial chromosomes from the same or different organisms, tissues, cells or a combination; one or more chromosome fragments from the same or different organisms, tissues, cells or a combination; one or more artificial chromosomes; one or more yeast artificial chromosomes; one or more bacterial artificial chromosomes; one or more cosmids; or any combination of these.

Oligonucleotide Synthesis

Primers, detection probes, address probes, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method. Solid phase chemical synthesis of DNA fragments is routinely performed using protected nucleoside cyanoethyl phosphoramidites (S. L. Beaucage et al. (1981) Tetrahedron Lett. 22:1859). In this approach, the 3'-hydroxyl group of an initial 5'-protected nucleoside is first covalently attached to the polymer support (R. C. Pless et al. (1975) Nucleic Acids Res. 2:773 (1975)). Synthesis of the oligonucleotide then proceeds by deprotection of the 5'-hydroxyl group of the attached nucleoside, followed by coupling of an incoming nucleoside-3'-phosphoramidite to the deprotected hydroxyl group (M. D. Matteucci et a. (1981) J. Am. Chem. Soc. 103:3185). The resulting phosphite triester is finally oxidized to a phosphorotriester to complete the internucleotide bond (R. L. Letsinger et al. (1976) J. Am. Chem. Soc. 9:3655). Alternatively, the synthesis of phosphorothioate linkages can be carried out by sulfurization of the phosphite triester. Several chemicals can be used to perform this reaction, among them 3H-1,2-benzodithiole-3-one, 1,1-dioxide (R. P. Iyer, W. Egan, J. B. Regan, and S. L. Beaucage, J. Am. Chem. Soc., 1990, 112, 1253-1254). The steps of deprotection, coupling and oxidation are repeated until an oligonucleotide of the desired length and sequence is obtained. Other methods exist to generate oligonucleotides such as the H-phosphonate method (Hall et al, (1957) J. Chem. Soc., 3291-3296) or the phosphotriester method as described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994). Other forms of oligonucleotide synthesis are described in U.S. Pat. No. 6,294,664 and U.S. Pat. No. 6,291,669.

The nucleotide sequence of an oligonucleotide is generally determined by the sequential order in which subunits of subunit blocks are added to the oligonucleotide chain during synthesis. Each round of addition can involve a different, specific nucleotide precursor, or a mixture of one or more different nucleotide precursors. For the disclosed primers of specific sequence, specific nucleotide precursors would be added sequentially.

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807-

10815 (1995), McGraw et al., *Biotechniques* 8:674-678 (1990), and Rychlik et al., *Nucleic Acids Res.* 18:6409-6412 (1990).

So long as their relevant function is maintained, primers, detection probes, address probes, and any other oligonucleotides can be made up of or include modified nucleotides (nucleotide analogs). Many modified nucleotides are known and can be used in oligonucleotides, and are disclosed elsewhere herein.

Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for amplification of nucleic acid samples, the kit comprising cooperative nucleic acids and a DNA polymerase. The kits also can contain nucleotides, buffers, detection probes, fluorescent change probes, lysis solutions, stabilization solutions, denaturation solutions, or a combination.

Uses

The disclosed method and compositions are applicable to numerous areas including, but not limited to, analysis of nucleic acids present in cells (for example, analysis of genomic DNA in cells), disease detection, mutation detection, gene discovery, gene mapping (molecular haplotyping), and agricultural research. Particularly useful is whole genome amplification. Other uses include, for example, detection of nucleic acids in cells and on genomic DNA arrays; molecular haplotyping; mutation detection; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

Amplification

Amplification methods suitable for use with the present methods include, for example, polymerase chain reaction (PCR), reverse transcription PCR(RT-PCR), ligase chain reaction (LCR), transcription-based amplification system (TAS), nucleic acid sequence based amplification (NASBA) reaction, self-sustained sequence replication (3SR), strand displacement amplification (SDA) reaction, boomerang DNA amplification (BDA), Q-beta replication: or isothermal nucleic acid sequence based amplification. These methods of amplification each described briefly below and are well-known in the art.

PCR is a technique for making many copies of a specific template DNA sequence. The reaction consists of multiple amplification cycles and is initiated using a pair of primer oligonucleotides that hybridize to the 5' and 3' ends of the sequence to be copied. The amplification cycle includes an initial denaturation, and up to 50 cycles of annealing, strand elongation (or extension) and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al, Journal of Clinical Microbiology, 33(3):556-561 (1995). Briefly, a PCR reaction mixture includes two specific primers, dNTPs, Taq polymerase, and 1×PCR Buffer, which is amplified using a thermal cycler. Cycling parameters can be varied, depending on, for example, the melting temperature of the primer or the length of nucleic acids to be extended. The skilled artisan is capable of designing and preparing primers that are appropriate for amplifying a target sequence. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill and include considerations described herein. For example, the length of a short nucleic acid or oligonucleotide can relate to its hybridization specificity or selectivity.

Real time PCR is PCR-based amplification method in which PCR products are detected in real time, that is, the accumulation of PCR products can be determined at each cycle. An example of Real Time PCR is performed using TaqMan probes in combination with a suitable amplification/analyzer such as Applied Biosystems (ABI) Prism 7900HT Sequence Detection System, which is a high-throughput real-time PCR system. Briefly, TaqMan probes specific for the amplified target sequence are included in the PCR amplification reaction. These probes contain a reporter dye at the 5' end and a quencher dye at the 3' end. Probes hybridizing to different target sequences are conjugated with a different fluorescent reporter dye. In this way, more than one target sequence can be assayed for in the same reaction vessel. During PCR, the fluorescently labeled probes bind specifically to their respective target sequences; the 5' nuclease activity of Taq polymerase cleaves the reporter dye from the probe and a fluorescent signal is generated. The increase in fluorescence signal is detected only if the target sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation. Real Time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually.

"RT-PCR" as used herein refers to the combination of reverse transcription and PCR in a single assay. "Reverse transcription" is a process whereby an RNA template is transcribed into a DNA molecule by a reverse transcriptase enzyme. Thus, "reverse transcriptase" describes a class of polymerases characterized as RNA-dependent DNA polymerases, that is, such polymerases use an RNA template to synthesize a DNA molecule. Historically, reverse transcriptases have been used to reverse-transcribe mRNA into cDNA. However, reverse transcriptases can be used to reverse-transcribe other types of RNAs such as viral genomic RNA or viral sub-genomic RNA. Standard reverse transcriptases include Maloney Murine Leukemia Virus Reverse Transcriptase (MoMuLV RT) and Avian myoblastosis virus (AMV). These enzymes have 5'→3' RNA-dependent DNA polymerase activity, 5'→3' DNA-dependent DNA polymerase activity, and RNase H activity. However, unlike many DNA-dependent DNA polymerases, these enzymes lack 3'→5' exonuclease activity necessary for "proofreading," (i.e., correcting errors made during transcription).

After a DNA copy of an RNA has been prepared, the DNA copy may be subjected to various DNA amplification methods such as PCR.

LCR is a method of DNA amplification similar to PCR, except that it uses four primers instead of two and uses the enzyme ligase to ligate or join two segments of DNA. LCR can be performed as according to Moore et al., Journal of Clinical Microbiology 36(4)1028-1031 (1998). Briefly, an LCR reaction mixture contains two pair of primers, dNTP, DNA ligase and DNA polymerase representing about 90 µl, to which is added 100 µl of isolated nucleic acid from the target organism. Amplification is performed in a thermal cycler (e.g., LCx of Abbott Labs, North Chicago, Ill.).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., PNAS 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 37° C. for approximately 25 minutes for the synthesis of RNA. The above steps are then repeated. Alternatively, after the initial cDNA synthesis, both RT and RNA polymerase are added following a 1 minute 100° C. denaturation followed by an RNA elongation of approximately 30 minutes at 37° C. TAS can be also be performed on solid phase as according to Wylie et al., Journal of Clinical Microbiology, 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 µl TMA reaction mixture is placed in a tube, 200 µl oil reagent is added and amplification is accomplished by incubation at 42° C. in a waterbath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian mycloblastosis virus (AMV) reverse transcriptase, RNase H and T7 RNA polymerase are used. This method can be performed as according to Heim, et al., Nucleic Acids Res., 26(9):2250-2251 (1998). Briefly, an NASBA reaction mixture contains two specific primers, dNTP, NTP, 6.4 U of AMV reverse transcriptase, 0.08 U of *Escherichia coli* Rnase H, and 32 U of T7 RNA polymerase. The amplification is carried out for 120 min at 41° C. in a total volume of 201.

In a related method, self-sustained sequence-replication (3SR) reaction, isothermal amplification of target DNA or RNA sequences in vitro using three enzymatic activities: reverse transcriptase, DNA-dependent RNA polymerase and *Escherichia coli* ribonuclease H. This method may be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3SR, the amplified RNA is obtained in a purer form compared with the 3-enzyme 3SR (Gebinoga & Oehlenschlager European Journal of Biochemistry, 235: 256-261, 1996).

SDA is an isothermal nucleic acid amplification method. A primer containing a restriction site is annealed to the template. Amplification primers are then annealed to 5' adjacent sequences (forming a nick) and amplification is started at a fixed temperature. Newly synthesized DNA strands are nicked by a restriction enzyme and the polymerase amplification begins again, displacing the newly synthesized strands. SDA can be performed as according to Walker, et al., PNAS, 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo.sup.-Klenow polymerase). The sample mixture is heated 95° C. for 4 minutes to denature target DNA prior to addition of the enzymes. After addition of the two enzymes, amplification is carried out for 120 min. at 37° C. in a total volume of 50 µl. Then, the reaction is terminated by heating for 2 minutes at 95° C.

Boomerang DNA amplification (BDA) is a method in which the polymerase begins extension from a single primer-binding site and then makes a loop around to the other strand, eventually returning to the original priming site on the DNA. BDA is differs from PCR through its use of a single primer. This method involves an endonuclease digestion of a sample DNA, producing discrete DNA fragments with sticky ends, ligating the fragments to "adapter" polynucleotides (comprised of a ligatable end and first and second self-complementary sequences separated by a spacer sequence) thereby forming ligated duplexes. The ligated duplexes are denatured to form templates to which an oligonucleotide primer anneals at a specific sequence within the target or marker sequence of interest. The primer is extended with a DNA polymerase to form duplex products followed by denaturation of the duplex products. Subsequent multiple cycles of annealing, extending, and denaturing are performed to achieve the desired degree of amplification (U.S. Pat. No. 5,470,724).

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi Trends Biotechnol. 1991 9(2):53-8, 1991).

A variety of amplification enzymes are well known in the art and include, for example, DNA polymerase, RNA polymerase, reverse transcriptase, Q-beta replicase, thermostable DNA and RNA polymerases. Because these and other amplification reactions are catalyzed by enzymes, in a single step assay that the nucleic acid releasing reagents and the detection reagents should not be potential inhibitors of amplification enzymes if the ultimate detection is to be amplification based.

Amplification of the nucleic acid molecules in a nucleic acid sample can result replication of at least 0.01% of the nucleic acid sequences in the nucleic acid sample, at least 0.1% of the nucleic acid sequences in the nucleic acid sample, at least 1% of the nucleic acid sequences in the nucleic acid sample, at least 5% of the nucleic acid sequences in the nucleic acid sample, at least 10% of the nucleic acid sequences in the nucleic acid sample, at least 20% of the nucleic acid sequences in the nucleic acid sample, at least 30% of the nucleic acid sequences in the nucleic acid sample, at least 40% of the nucleic acid sequences in the nucleic acid sample, at least 50% of the nucleic acid sequences in the nucleic acid sample, at least 60% of the nucleic acid sequences in the nucleic acid sample, at least 70% of the nucleic acid sequences in the nucleic acid sample, at least 80% of the nucleic acid sequences in the nucleic acid sample, at least 90% of the nucleic acid sequences in the nucleic acid sample, at least 95% of the nucleic acid sequences in the nucleic acid sample, at least 96% of the nucleic acid sequences in the nucleic acid sample, at least 97% of the nucleic acid sequences in the nucleic acid sample, at least 98% of the nucleic acid sequences in the nucleic acid sample, or at least 99% of the nucleic acid sequences in the nucleic acid sample.

The various sequence representations described above and elsewhere herein can be, for example, for 1 target sequence, 2 target sequences, 3 target sequences, 4 target sequences, 5 target sequences, 6 target sequences, 7 target sequences, 8 target sequences, 9 target sequences, 10 target sequences, 11 target sequences, 12 target sequences, 13 target sequences, 14 target sequences, 15 target sequences, 16 target sequences, 17 target sequences, 18 target sequences, 19 target sequences, 20 target sequences, 25 target sequences, 30 target sequences, 40 target sequences, 50 target sequences, 75 target sequences, or 100 target sequences. The sequence representation can be, for example, for at least 1 target sequence, at least 2 target sequences, at least 3 target sequences, at least 4 target sequences, at least 5 target sequences, at least 6 target sequences, at least 7 target sequences, at least 8 target sequences, at least 9 target sequences, at least 10 target sequences, at least 11 target sequences, at least 12 target sequences, at least 13 target sequences, at least 14 target sequences, at least 15 target sequences, at least 16 target sequences, at least 17 target sequences, at least 18 target sequences, at least 19 target sequences, at least 20 target sequences, at least 25 target sequences, at least 30 target sequences, at least 40 target sequences, at least 50 target sequences, at least 75 target sequences, or at least 100 target sequences.

The sequence representation can be, for example, for 1 target sequence, 2 different target sequences, 3 different target sequences, 4 different target sequences, 5 different target sequences, 6 different target sequences, 7 different target sequences, 8 different target sequences, 9 different target sequences, 10 different target sequences, 11 different target sequences, 12 different target sequences, 13 different target sequences, 14 different target sequences, 15 different target sequences, 16 different target sequences, 17 different target sequences, 18 different target sequences, 19 different target sequences, 20 different target sequences, 25 different target sequences, 30 different target sequences, 40 different target sequences, 50 different target sequences, 75 different target sequences, or 100 different target sequences. The sequence representation can be, for example, for at least 1 target sequence, at least 2 different target sequences, at least 3 different target sequences, at least 4 different target sequences, at least 5 different target sequences, at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

Detection

Products of amplification can be detected using any nucleic acid detection technique. For real-time detection, the amplification products and the progress of amplification are detected during amplification. Real-time detection is usefully accomplished using one or more or one or a combination of fluorescent change probes and fluorescent change primers. Other detection techniques can be used, either alone or in combination with real-timer detection and/or detection involving fluorescent change probes and primers. Many techniques are known for detecting nucleic acids. The nucleotide sequence of the amplified sequences also can be determined using any suitable technique.

For example, nucleic acid product may be detected by any of a variety of well-known methods, for example, electrophoresis (e.g., gel electrophoresis or capillary electrophoresis). Amplified fragments may be subjected to further methods of detecting, for example, variant sequences (e.g., single nucleotide polymorphisms (SNPs)). An exemplary method is single nucleotide primer extension (Lindblad-Toh et al., Large-scale discovery and genotyping of single-nucleotide polymorphisms in the mouse. Nature Genet. 2000 April; 24(4):381-6). In this reaction, an oligonucleotide primer is designed to have a 3' end that is one nucleotide 5' to a specific mutation site. In some embodiments, the extension primers are labeled with a tag or a member of a binding pair to allow the capture of the primer on solid phase. In particular embodiments, the primers may be tagged with varying lengths of nonspecific polynucleotides (e.g., poly-GACT) to allow multiplex detection of preferably 2 or more, more preferably 3 or more, 4 or more, 5 or more, even 10 or more different mutations (polymorphisms) in a single reaction. The primer hybridizes to the PCR amplicon in the presence of one or more labeled ddNTPs and a DNA polymerase. The polymerase extends the primer by one nucleotide, adding a single, labeled ddNTP to the 3' end of the extension primer. The addition of a dideoxy nucleotide terminates chain elongation. If more than one dideoxynucleotide (e.g., ddATP, ddGTP, ddCTP, ddTTP, ddUTP, etc.) is used in a reaction, one or more can be labeled. If multiple labels are used, the labels can be distinguishable e.g., each is labeled with a different fluorescent colored dye. The products are labeled oligonucleotides, each one of which may be detected based on its label. Further methods of detecting variant sequences include the READIT SNP Genotyping System (Promega Corporation, Madison Wis.) and oligonucleotide ligation assays.

EXAMPLES

Example I: Primers for Malaria

Capture sequences were designed with a Tm of 2 to 5° C. below the reaction temperature of 55° C. Primer sequences were designed with a Tm of around 10° C. below the reaction temperature. Linkers attaching the 5' end of the primer to the 5' end of the probe were used (see FIG. 5).

```
                                            (SEQ ID NO: 1)
3' TCGCTACGCA 5' [Spacer 18][Spacer 18]
[Spacer 18] 5' [T(FAM)]

(SEQ ID NO: 2)
ACGGTGAACTCTCA 3' [DABCYL] 3'

(SEQ ID NO: 3)
3' TCGCTACGCA 5' [Spacer 18][Spacer 18]
[Spacer 18][Spacer 18] 5'

(SEQ ID NO: 4)
ACGGTGAACTCTCA 3' [DABCYL] 3'

(SEQ ID NO: 5)
3' TCGCTACGCA 5' [Spacer 18][Spacer 18]
[Spacer 18][Spacer 18] 5'

(SEQ ID NO: 6)
TCTAACGGTGAACTC 3' [DABCYL] 3'
```

A regular primer was used for the reverse primer and a control using just a regular primer for the forward primer and a Rapid Probe for detection was used. The primers were run in a real-time PCR reaction with GoTaq DNA master mix with final MgCl2 concentration of 5 mM. Final primer concentration was 250 nM. Reaction conditions were 95° C. for 20 s followed by 45 cycles of 95° C. for is and 55° C. for 20 s.

All three cooperative primers generated detectable amplicon and had a detectable signal from the labeled capture sequence. The cooperative primer with no distance between the primer and capture sequence amplified less efficiently than the others.

The same real-time PCR reaction was repeated with an annealing/extension temperature of 50° C. The signal generated from the labeled capture sequence was greater for all three cooperative primers. Real-time PCR efficiency did not appear to improve at the lower temperature.

Example 2: High Tm Capture Sequences

Labeled capture sequences were designed with a Tm of 7 to 10° C. above the reaction temperature of 55° C. The reverse cooperative primer was made with an unlabeled capture sequence with a Tm of about 2° C. less than the reaction temperature. Primer sequences were designed with a Tm of around 7 to 10° C. below the reaction temperature.

```
                                            (SEQ ID NO: 7)
3' TCGCTACGCA 5' [Spacer 18][Spacer 18]
[Spacer 18] 5' [T(FAM)]

(SEQ ID NO: 8)
ACGGTGAACTCTCATTCCA 3' [DABCYL] 3'

(SEQ ID NO: 9)
3' TCGCTACGCA 5' [Spacer 18][Spacer 18]
[Spacer 18] 5' [(FAM)]

(SEQ ID NO: 10)
ACGGTGAACTCTCATTCCA CCG 3' [DABCYL] 3'

(SEQ ID NO: 11)
3' ATTGACATACCTGC 5' [Spacer 18][Spacer 18]
[Spacer 18] 5'

(SEQ ID NO: 12)
AGCAAGTGGAATGTT [Phos] 3'
```

The primers were run in a real-time PCR reaction with GoTaq DNA master mix with final MgCl2 concentration of 5 mM. Final primer concentration was 250 nM. Reaction conditions were 95° C. for 20 s followed by 50 cycles of 95° C. for is and 55° C. for 20 s. The real-time PCR was also repeated with an extension step of 40 s.

The cooperative primers with High Tm capture sequences had a similar amplification efficiency and change in fluorescence to the low Tm capture sequences from Example 1. Increasing the extension time did not appear to increase amplification efficiency.

Example 3: Elimination of Primer-Dimers

Primer-dimers were synthesized for the cooperative primers and the normal primers. Either 0, 600, 6,000 or 600,000 primer-dimers were spiked into a reaction containing 60 copies of Malaria DNA. The primers were run in a real-time PCR reaction with GoTaq DNA master mix with final MgCl2 concentration of 5 mM. Final primer concentration was 250 nM. Reaction conditions were 95° C. for 20 s followed by 50 cycles of 95° C. for is and 55° C. for 20 s.

The control with normal primers had easily visible positives when no primer-dimers were spiked in. However, with as few as 600 primer-dimers spiked in, the signal disappeared resulting in false negatives. In contrast, the cooperative primers had no signal dampening or loss of amplification product with even as many as 600,000 primer-dimers spiked in.

When a 2.2% Lonza flashgel was run with the PCR products, the gel confirmed the fact that no primer-dimers were amplified for the cooperative primers. However, the normal primers clearly amplified the primer-dimers rather than the Malaria DNA, resulting in false negatives.

Example 4: Cooperative Primers with Detection Mechanism on the Primer

Cooperative Primers with a detection mechanism on the primer were made:

```
                                            (SEQ ID NO: 13)
3' [Spacer 3] TTGTAAGGTGAACGA 5'

(SEQ ID NO: 46)
5' [Spacer 18][T(FAM)] actgtatgg (SEQ ID NO: 14)
[T(BHQ-1)][Spacer 9] CGTCCATACAGTTA 3'

(SEQ ID NO: 15)
3' [Spacer 3] TTGTAAGGTGAACGA 5'

(SEQ ID NO: 47)
5' [Spacer 9][Spacer 18][T(FAM)] atggacg (SEQ ID NO: 16)
[T(BHQ-1)][Spacer 9)] CGTCCATACAGTTA 3'

(SEQ ID NO: 17)
3' [Spacer 3] TTGTAAGGTGAACGA 5'

(SEQ ID NO: 48)
5' [T(FAM][Spacer 3] taactgtatg (SEQ ID NO: 18)
[T(FAM)][Spacer 18] CGTCCATACAGTTA 3'

(SEQ ID NO: 19)
3' [Spacer 3] TTGTAAGGTGAACGA 5'
```

-continued

[Spacer 9][T(FAM)] actgtatgg (SEQ ID NO: 49)

[T)BHQ-10)[Spacer 18] CGTCCATACAGTTA 3' (SEQ ID NO: 20)

3' [Spacer 3] AGATTGTAAGGTGAACGA 5' (SEQ ID NO: 21)

5' [Spacer 18][T(FAM)] actgtatgg (SEQ ID NO: 65)

[T(BHQ-1)][Spacer 9] CGTCCATACAGTTA 3' (SEQ ID NO: 22)

3' [Spacer 3] TTGTAAGGTGAACGA 5' (SEQ ID NO: 23)

5' [Spacer 18][T(FAM)] actgtatgg (SEQ ID NO: 66)

[T(BHQ-1)][Spacer 9 ]CGTCCATACAGTTAT 3' (SEQ ID NO: 24)

Example 5: Labeling the Capture Sequence

*P. falciparum* real-time PCR was run by making a master mix with 250 nM final concentration of each primer (either PfcF inv, PfcF inv62, PfcF inv62HP or PfcF with PfcR), 5 mM final concentration of MgCl2 and an additional 0.25 U/reaction of GoTaq polymerase (Promega) in GoTaq Colorless Master Mix (Promega). 5,000,000, 600,000, 50,000, 500 or 0 copies of template were added to each reaction. The reaction was run on the ABI StepOne and included a 20 s denature step at 95° C. followed by 45 cycles of 95° C. for 1 s and 55° C. for 20 s. Each reaction was run in duplicate.

Having demonstrated that cooperative primers are capable of efficient amplification and can eliminate interference from primer-dimers, we attempted to incorporate a probe into the primer. This was done by labeling the capture sequence. First, inverted primers were attached to the 5' end of capture sequences having Tm's both below and above the reaction temperature, including capture sequences with hairpin formation to encourage greater quenching of the fluorophore (Pf cF inv, Pf cF inv 62 and Pf cF inv 62HP). However, very little signal was observed from these primers and electrophoretic gels showed that very few of the primers were cleaving the capture sequence (FIG. 8—the barely visible bands below the amplicon of the cooperative primers).

Figure 8:
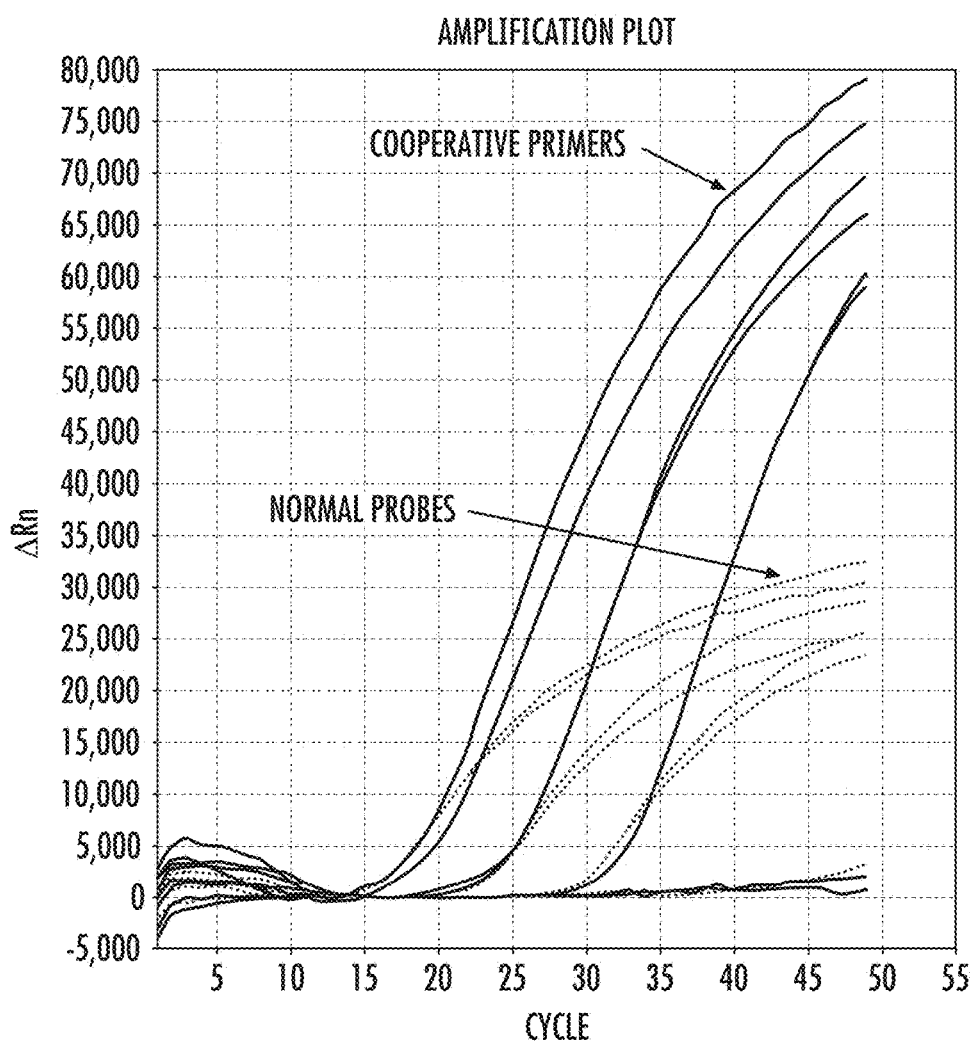
FIG. 8 shows cooperative primers with integrated probes. Labeled cooperative primers or normal hybridization probes were used for real time detection of 5,000,000, 50,000, 500 or 0 copies P. falciparum template. Labeled capture sequences in cooperative primers had a fluorescent signal 2.5× higher than normal hybridization probes, even though the capture sequence had a Tm below the reaction temperature.

It was believed that conformational stain from the linker was lifting the 5' end of the capture sequence and causing the polymerase to displace the sequence rather than cleave it. Consequently, if the strain was moved from the 5' end to the 3' end (e.g. by changing where the linker was attached), the polymerase might cleave the capture sequence with greater efficiency. Upon testing this hypothesis the fluorescent signal rose dramatically (FIG. 8). Even though the labeled capture sequence had a Tm below the reaction temperature, the signal was still 2.5 times higher than the signal from normal hybridization probes.

Example 6: SNP Differentiation

*M. tuberculosis* real-time PCR for the D516V mutation in the rpoB gene conferring rifampicin resistance was run by making a master mix with 250 nM final concentration of each primer/probe (MTb cF, MTb P, and one of MTb cR1, MTb cR2, MTb cR3, MTb cR4, MTb cR5, MTb cR6, MTb cR7, MTb cR8 or MTb cR9), 5 mM final concentration of MgCl2 and an additional 0.25 U/reaction of GoTaq polymerase (Promega) in GoTaq Colorless Master Mix (Promega). 50,000 copies of template (MTb WT or MTb D516V) were added to each reaction. Each reaction was run in duplicate. The reaction was run on the ABI 7500 and included a 20 s denature step at 95° C. followed by 45 cycles of 95° C. for 3 s and 55° C. for 3 s. The Ct's were automatically determined by the machine with a threshold of 10,000 and the ΔRn was taken from cycle 45 of the exported data.

Figure 9A:
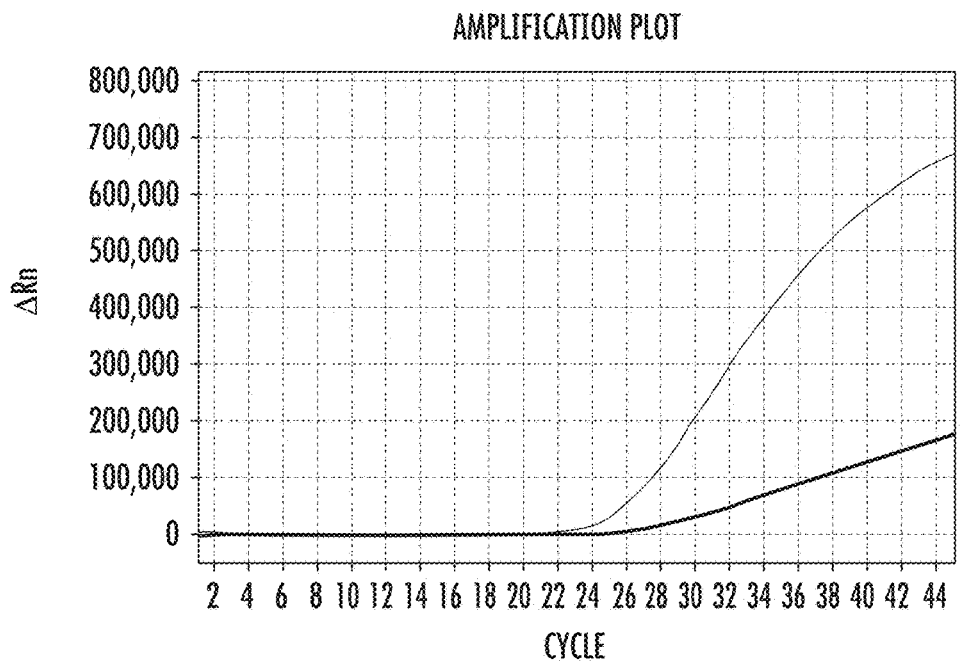
FIGS. 9A-B show SNP differentiation with cooperative primers. Cooperative Primers differentiate between Tuberculosis Complex with the rpoB D516V SNP causing rifampicin resistance and without the SNP using probe based differentiation with the SNP under the capture sequence (9A) and the ARMS based method with the SNP under the 3' end of the primer (9B).
Figure 9B:
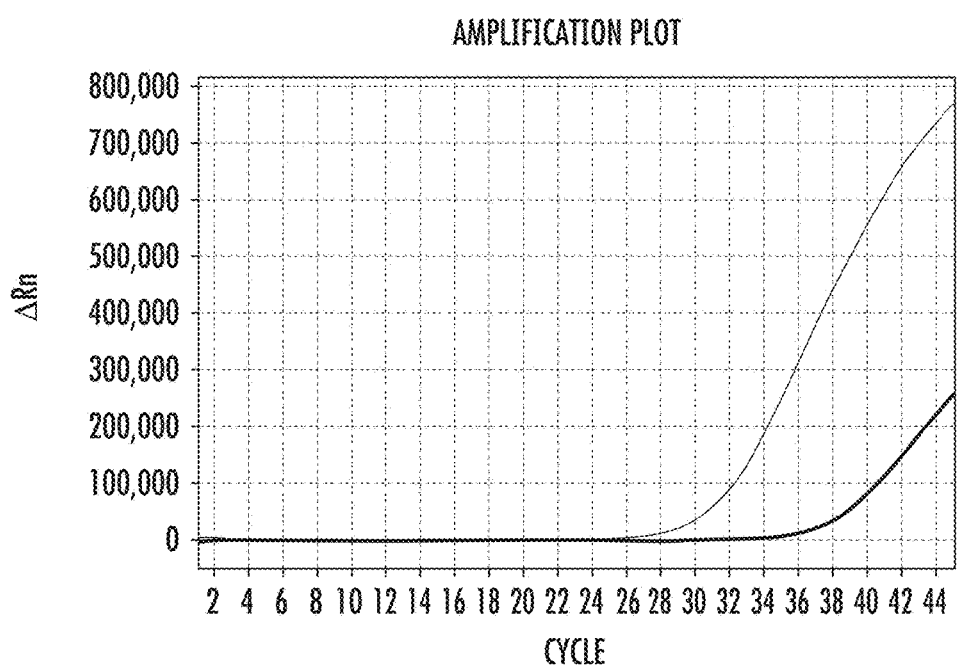

Finally, the ability of these efficient, primer-dimer free, cooperative primers to differentiate SNP's was analyzed. Cooperative Primers were designed to the rpoB gene D516V mutation, which is present in up to 7.4% of rifampicin resistant *M. tuberculosis* isolates in India. Two different strategies were employed: 1) the ARMS method and 2) labeled capture sequence differentiation. Both methods resulted in the ability to differentiate SNP's similar to standard primers and probes (FIG. 9 and data summary in Table 1).

For the probe based method, cooperative primer MTb cR6 gave the best ratio of fluorescent signals between the mutant and wild type strains. For the ARMS based method, MTb cR8 gave the best difference in Ct values. Both are shown in FIG. 9.

TABLE 1

| D516V primer name | Method | Primer ΔTm | Probe ΔTm | ΔCt | ΔRnVar/ ΔRnWT |
|---|---|---|---|---|---|
| MTb cR1 | Probe | (4.1) | 4.5 | 1.68 | 3.01 |
| MTb cR2 | Probe | (4.1) | (2.5) | 4.79 | 3.35 |
| MTb cR5 | Probe | (6.6) | (2.5) | 4.83 | 1.89 |
| MTb cR6 | Probe | (4.1) | (7.1) | 3.83 | 3.67 |
| MTb cR7 | Probe | (4.1) | (11.7) | 5.30 | 3.62 |
| MTb cR3 | ARMS | (6.3) | 4.3 | 4.43 | n/a |
| MTb cR4 | ARMS | (10.2) | 4.3 | 5.99 | n/a |
| MTb cR8 | ARMS | (20.2) | 4.3 | 7.57 | n/a |
| MTb cR9 | ARMS | (25.5) | 4.3 | 7.13 | n/a |

Table 1 Shows a Summary of SNP Differentiation Methods.

Each primer is listed together with whether it uses ARMS or probe (labeled capture sequence) based differentiation, the number of degrees the predicted Tm for the primer or probe is above or below the reaction temperature (values below the reaction temperature are in red font and in parenthesis), the difference between mutant and wild type Ct values, and the ratio of the mutant and wild type fluorescence.

Sequences 5' to 3'

Beta Actin (Amplification Efficiency)
Normal Primers/Probes b-act P　　　　　　　　[FAM] TGTGGCCGAGGACTTTGAcggc [BHQ1] (SEQ ID NO: 25)

Cooperative

-continued

| Sequences 5' to 3' |  |
|---|---|
| Primers | |
| b-act cF | 3' AGTGGCAAGGTC 5' (SEQ ID NO: 26) [Sp18][Sp18][Sp18]<br>5' GGTGACAGCAGTC [Sp3] 3'(SEQ ID NO: 27) |
| b-act cR | 3' TAGGATTTTCGGTG 5' (SEQ ID NO: 28) [Sp18][Sp18][Sp18]<br>5' GCAAGGGACTTCC [Sp3] 3' (SEQ ID NO: 29) |
| Templates | |
| Beta actin | AGGATTTAAAAACTGGAACGGTGAAGGTGACAGCAGTCGGTTGG<br>AGCGAGCATCCCCCAAAGTTCACAATGTGGCCGAGGACTTTGATTG<br>CACATTGTTGTTTTTTAATAGTCATTCCAAATATGAGATGCGTTGTT<br>ACAGGAAGTCCCTTGCCATCCTAAAAGCCACCCCA (SEQ ID NO: 30) |
| *P. Falciparum* (Impact of Primer-Dimers and Probe Selection)<br>Normal Primers/Probes | |
| Pf nF | CGCATCGCTTCTAACGGTGA (SEQ ID NO: 31) |
| Pf nR | GAAGCAAACACTAGCGGTGGAA (SEQ ID NO: 32) |
| Pf P | [FAM] ACTCTCATTCCAATGGAACCTTGTTCAAGTTCAAAccattggaa [DABC]<br>(SEQ ID NO: 33) |
| Cooperative Primers/Probes | |
| Pf cF inv | 3' TCGCTACGCA (SEQ ID NO: 34) 5' [Sp18][Sp18][Sp18] 5' [FAM]<br>ACGGTGAACTCTCA [DABC] 3' (SEQ ID NO: 35) |
| Pf cF inv 62 | 3' TCGCTACGCA 5' (SEQ ID NO: 36) [Sp18][Sp18][Sp18] 5' [T(FAM)] A<br>CGGTGAACTCTCATTCCA 3' (SEQ ID NO: 37) |
| Pf cF inv 62HP | 3' TCGCTACGCA 5' (SEQ ID NO: 38) [Sp18][Sp18][Sp18] 5' [T(FAM)]<br>ACGGTGAACTCTCATTCCA ccg [DABC] 3' (SEQ ID NO: 39) |
| Pf cF | [FAM] ACGGTGAACTCTCA [Sp18][Sp18][Sp18][Sp18][Sp18][Sp18]<br>ACGCATCGCT (SEQ ID NO: 40) |
| Pf cR inv | 3' ATTGACATACCTGC 5' (SEQ ID NO: 67) [Sp18][Sp18][Sp18] 5' AGCAAGT<br>GGAATGTT [Phos] 3' (SEQ ID NO: 41) |
| Low Tm Primers minus Capture Sequence | |
| Pf Low Tm | F ACGCATCGCT (SEQ ID NO: 42) |
| Pf Low Tm | R CGTCCATACAGTTA (SEQ ID NO: 43) |
| Templates | |
| Normal<br>Primer-Dimer | GAAGCAAACACTAGCGGTGGAATCACCGTTAGAAGCGATGCG<br>(SEQ ID NO: 44) |
| Cooperative<br>Primer-Dimer | CGTCCATACAGTTA AGCGATGCGT (SEQ ID NO: 45) |
| *P. Falciparum* | CCAGCTCACGCATCGCTTCTAACGGTGAACTCTCATTCCAATGGAA<br>CCTTGTTCAAGTTCAAATAGATTGGTAAGGTATAGTGTTTACTATC<br>AAATGAAACAATGTGTTCCACCGCTAGTGTTTGCTCTAACATTCCAC<br>TTGCTTATAACTGTATGGACG (SEQ ID NO: 50) |
| *M. Tuberculosis* (SNP Differentiation)<br>Normal Primers/Probes | |
| MTb P | [FAM] CGCCGCGATCAAGGAGTTCgcg [BHQ1] (SEQ ID NO: 51) |
| Cooperative Primers/Probes | |
| MTb cF | 3' ACACTAGCGGAG 5' (SEQ ID NO: 52) [Sp18][Sp18][Sp18]<br>5' CGCAGACGTTGAT [Phos] 3'(SEQ ID NO: 53) |
| MTb cR1 | [CF 560] TGGaCCATGAATTGGCT [BHQ1] [Sp18][Sp18][Sp18][Sp18]<br>[Sp18][Sp18] CAGCGGGTTGTT (SEQ ID NO: 54) |
| MTb cR2 | [CF 560] TGGaCCATGAATTGG [BHQ1] [Sp18][Sp18][Sp18][Sp18]<br>[Sp18][Sp18] CAGCGGGTTGTT (SEQ ID NO: 55) |
| MTb cR3 | [CF 560]CATGAATTGGCTCAGCTG [BHQ1] [Sp18][Sp18][Sp18][Sp18]<br>[Sp18][Sp18] GGGTTGTTCTGGa (SEQ ID NO: 56) |
| MTb cR4 | [CF 560]CATGAATTGGCTCAGCTG [BHQ1] [Sp18][Sp18][Sp18][Sp18]<br>[Sp18][Sp18] CGGGTTGTTCTaGa (SEQ ID NO: 57) |
| MTb cR5 | [CF 560]TGGaCCATGAATTGG [BHQ1] [Sp18][Sp18][Sp18][Sp18]<br>[Sp18][Sp18] AGCGGGTTGTT (SEQ ID NO: 58) |
| MTb cR6 | [CF 560]TGGaCCATGAATTG [BHQ1] [Sp18][Sp18][Sp18][Sp18]<br>[Sp18][Sp18] CAGCGGGTTGTT (SEQ ID NO: 59) |
| MTb cR7 | [CF 560]TGGaCCATGAATT [BHQ1] [Sp18][Sp18][Sp18]<br>[Sp18][Sp18][Sp18] CAGCGGGTTGTT (SEQ ID NO: 60) |

| Sequences 5' to 3' | |
|---|---|
| MTb cR8 | [CF 560] CATGAATTGGCTCAGCTG [BHQ1] [Sp18][Sp18][Sp18][Sp18] [Sp18][Sp18] GGGTTGTTCTcGa (SEQ ID NO: 61) |
| MTb cR9 | [CF 560]CATGAATTGGCTCAGCTG [BHQ1] [Sp18][Sp18][Sp18][Sp18] [Sp18][Sp18] GGGTTcTTCTGGa (SEQ ID NO: 62) |
| Templates | |
| MTb WT | CGTGGAGGCGATCACACCGCAGACGTTGATCAACATCCGGCCGGTGGT CGCCGCGATCAAGGAGTTCTTCGGCACCAGCCAGCTGAGCCAATTCAT GGACCAGAACAACCCGCTGTCGGGGTTGACCCACAAGCGCCGACTGTC GGCGCTGGGGCCCGGCGGTCTGTCACGTGAGCGTGCCGGGCTGGAGGT CCGCGA (SEQ ID NO: 63) |
| MTb D516V | CGTGGAGGCGATCACACCGCAGACGTTGATCAACATCCGGCCGGTGGT CGCCGCGATCAAGGAGTTCTTCGGCACCAGCCAGCTGAGCCAATTCA TGGTCCAGAACAACCCGCTGTCGGGGTTGACCCACAAGCGCCGACTGT CGGCGCTGGGGCCCGGCGGTCTGTCACGTGAGCGTGCCGGGCTGGAGG TCCGCGA (SEQ ID NO: 64) |

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a primer" includes a plurality of such primers, reference to "the primer" is a reference to one or more primers and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are specifically incorporated by reference. Nothing herein is to be construed as an admission that the present invention is not entitled to antedate such disclosure by virtue of prior invention.

Those skilled in the art will recognize, or be able to ascertain using no more than routine experimentation, many equivalents to the specific embodiments of the method and compositions described herein. Such equivalents are intended to be encompassed by the following claims.

I claim:

1. A method for synthesizing a nucleic acid, the method comprising:
   a. contacting a target nucleic acid with
   a cooperative nucleic acid molecule comprising:
      i. a first nucleic acid sequence, wherein the first nucleic acid sequence is complementary to a first region of a target nucleic acid, and wherein the first nucleic acid sequence is extendable on the 3' end;
      ii. a second nucleic acid sequence, wherein the second nucleic acid sequence is complementary to a second region of the target nucleic acid, such that it hybridizes to the target nucleic acid downstream from the 3' end of the first nucleic acid sequence;
      iii. a linker connecting said first and second nucleic acid sequences in a manner that allows both the said first nucleic acid sequence to hybridize to the target and extend on the 3' end and the second nucleic acid sequences to hybridize to the target at the same time;
   b. and providing conditions appropriate for nucleic acid synthesis wherein the polymerase extends from the 3' end of the first nucleic acid sequence through the second nucleic acid sequence, thereby synthesizing a nucleic acid.

2. The method of claim 1 wherein the cooperative nucleic acid molecule comprises a label.

3. The method of claim 1, wherein more than one cooperative nucleic acid molecule with different sequences are provided.

4. The method of claim 1, wherein the first nucleic acid molecule will not hybridize to the target without the second nucleic acid molecule hybridizing to the target.

5. The method of claim 1, wherein the second nucleic acid molecule will not hybridize to the target without the first nucleic acid molecule hybridizing to the target.

6. The method of claim 1, wherein neither the first nor the second nucleic acid molecule will hybridize to the target without the other hybridizing to the target.

7. The method of claim 1, wherein effective melting temperature (Tm) of the first nucleic acid molecule is increased by at least 1° C. as compared to the Tm of an isolated first nucleic acid sequence without the second nucleic acid sequence attached to it.

8. The method claim 1, wherein the second nucleic acid sequence comprises a label.

* * * * *